US006265417B1

(12) United States Patent
Carroll et al.

(10) Patent No.: US 6,265,417 B1
(45) Date of Patent: Jul. 24, 2001

(54) POTASSIUM CHANNEL OPENERS

(75) Inventors: William A. Carroll, Evanston; Irene Drizin, Wadsworth, both of IL (US); Mark W. Holladay, Tucson, AZ (US); James P. Sullivan, Deerfield; Henry Q. Zhang, Grayslake, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/206,055

(22) Filed: Dec. 4, 1998

Related U.S. Application Data

(63) Continuation-in-part of application No. 08/993,392, filed on Dec. 18, 1997, now abandoned.

(51) Int. Cl.[7] .................... A61K 31/47; A61K 31/4365; A61K 31/4709; C07D 215/36; C07D 495/04
(52) U.S. Cl. ................... 514/301; 514/299; 514/312; 546/112; 546/114; 546/153
(58) Field of Search ................... 546/114, 112, 546/153; 514/301, 312, 299

(56) References Cited

U.S. PATENT DOCUMENTS

| | | | |
|---|---|---|---|
| 4,532,248 | * 7/1985 | Franckowiak | 514/302 |
| 4,879,384 | 11/1989 | Schweuder | 546/114 |
| 5,270,308 | * 12/1993 | Shiraishi | 514/229.8 |
| 5,455,253 | * 10/1995 | Ohnmacht | 514/311 |

FOREIGN PATENT DOCUMENTS

| | | |
|---|---|---|
| 26 16 995 | 10/1977 | (DE) . |
| 2658804 | 7/1978 | (DE) . |
| 2747513 | 5/1979 | (DE) . |
| 0 145 956 | 6/1985 | (EP) . |
| 0 189 060 | 7/1986 | (EP) . |
| 0 241 281 | 10/1987 | (EP) . |
| 0 400 660 | 12/1990 | (EP) . |
| 0 462 696 | 12/1991 | (EP) . |
| 0539154 | 4/1993 | (EP) . |
| 0 705 830 | 4/1996 | (EP) . |
| 9408966 | 4/1994 | (WO) . |
| 96/02547 | 2/1996 | (WO) . |
| 99/31059 | 6/1999 | (WO) . |
| 00/24743 | 5/2000 | (WO) . |
| 00/51986 | 9/2000 | (WO) . |

OTHER PUBLICATIONS

Berge, S.M.; Journal Pharmaceutical Sciences; 66: 1 et seq. (1977).
Dodd, John H.; "Synthesis of Novel Cyclic Sulfone Dihydropyridines Facilitated by a Selective Ethyl Diazoacetate Ring Expansion"; *J. Heterocyclic Chem.* 27:1453–1456 (1990).

Freedman, Jonathon E. et al.; "ATP–sensitive Potassium Channels: Diverse Functions in the Central Nervous System"; *The Neuroscientist* 2:(3)145–152 (1996).
Gehlert, Donald R.; "ATP Sensitive Potassium Channels: Potential Drug Targets in Neuropsychopharmacology"; *Prog. Neuro–Psychopharmacol & Biol. Psychiat.* 18:1093–1102 (1994).
Gopalakrishnan, M. et al.; "ATP–Sensitive $K^+$ Channels: Pharmacologic Properties, Regulation, and Therapeutic Potential"; *Drug Development Research* 28:95–127 (1993).
Howe, Burton B. et al.; "Zeneca ZD6169: A Novel $K_{ATP}$ Channel Opener with in Vivo Selectivity for Urinary Bladder"; *The Journal of Pharmacology and Experimental Therapeutics* 274:884–890 (1995).
Klockner, V. and Isenberg, G.; Pflugers Arch; 405;329–339 (1985).
Lawson, K.; "Potassium Channel Activation: A Potential Therapeutic Approach?"; *Pharmacol Ther.* 70: (1) 39–63 (1996).
Nurse, D.E. et al.; Br. J. Urol.; vol. 68; pp. 27–31 (1991).
Quast et al; Mol. Pharmacol; vol. 43; pp. 474–481 (1993).
Spanswick, D. et al.; "Leptin inhibits hypothalamic neurons by activation of ATP–sensitive potassium channels"; *Nature* 390:521–25; (Dec. 4, 1997).
Dodd, J. H., et al., "Synthesis and Biological Properties of FWJ 22108, A Bronchoselective Calcium Channel Blocker", *Drug Design and Discovery*, 10:65–75 (1993).
Fenk, C. J., et al., "Synthesis of a Novel Cyclic Sulfone Dihydropyridine: An Investigation of the Isomerization Reaction Converting an Exocyclic Double Bond Isomer into a 1,4–Dihydropyridine", *J. Heterocyclic Chem.*, 31:351–355 (1993).
Moore, Jr., J. B., et al., "RWJ–22108—a novel airway tissue—selective calcium channel blocker", *Agents Actions*, 40:57–61 (1993).
Ritchie, D. M., et al., "Experimental Antiasthmatic Activity of FWJ 22108: A Bronchoselective Calcium Entry Blocker", *Int. Arch. Allergy Immunol.*, 100:274–282 (1993).

* cited by examiner

*Primary Examiner*—Evelyn Mei Huang
(74) *Attorney, Agent, or Firm*—Michael J. Ward

(57) ABSTRACT

Compounds having the formula

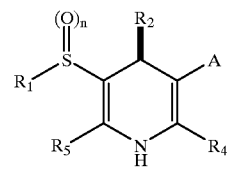

are useful in treating diseases prevented by or ameliorated with potassium channel openers. Also disclosed are potassium channel opening compositions and a method of opening potassium channels in a mammal.

13 Claims, No Drawings

POTASSIUM CHANNEL OPENERS

This application is a continuation-in-part of U.S. patent application Ser. No. 08/993,392 which was filed on Dec. 18, 1997 now abandoned.

TECHNICAL FIELD

Novel dihydropyridine compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions can be treated with therapeutic agents that open potassium channels. See K. Lawson, *Pharmacol. Ther.*, v. 70, pp. 39–63 (1996); D. R. Gehlert et al., *Prog. Neuro-Psychopharmacol & Biol. Psychiat.*, v. 18, pp. 1093–1102 (1994); M. Gopalakrishnan et al., *Drug Development Research*, v. 28, pp. 95–127 (1993); J. E. Freedman et al., *The Neuroscientist*, v. 2, pp. 145–152 (1996). Such diseases or conditions include asthma, epilepsy, hypertension, impotence, migraine, pain, urinary incontinence, stroke, Raynaud's Syndrome, eating disorders, functional bowel disorders, and neurodegeneration.

Potassium channel openers also act as smooth muscle relaxants. Because urinary incontinence can result from the spontaneous, uncontrolled contractions of the smooth muscle of the bladder, the ability of potassium channel openers to hyperpolarize bladder cells and relax bladder smooth muscle provides a method to ameliorate or prevent urinary incontinence.

WO 9408966 and EP 0539154 A1 disclose a group of acridinedione and quinolone compounds that are claimed useful in the treatment of urinary incontinence. These compounds belong to the larger general chemical class of dihydropyridines. The compounds of the present invention are chemically distinct from those of WO94/08966 and EP 0539154 A1 since they have at least one sulfonyl group attached to the 3-position of the dihydropyridine ring.

Dihydropyridines of differing chemical structure may possess a variety of biological activities. For example, U.S. Pat. No. 4,879,384 discloses a group of thiacycloalkeno[3,2-b]pyridines that belong to the dihydropyridine class and are calcium channel antagonists. The compounds of the present invention are chemically distinct from those of U.S. Pat. No. 4,879,384 since they do not have a carboxylic acid derivative attached to the 3-position of the dihydropyridine ring.

Thus, the compounds of the present invention are chemically distinct from the prior art, hyperpolarize cell membranes, open potassium channels, relax smooth muscle cells, inhibit bladder contractions and are useful for treating diseases that can be ameliorated by opening potassium channels.

SUMMARY OF THE INVENTION

The present invention relates to, the invention discloses a compound having Formula I

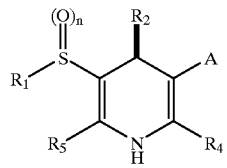

I or a pharmaceutically acceptable salt, ester, amide, or prodrug thereof wherein $R_1$ is alkyl;

$R_2$ is selected from the group consisting of aryl and heteroaryl;

the aryl or heteroaryl can be optionally substituted;

n is 0–2;

A is selected from the group consisting of hydrogen, alkyl, and —X—$R_3$;

$R_3$ is alkyl or haloalkyl;

X is —C(O)— or —S(O)$_p$— wherein p is 1–2;

$R_4$ and $R_5$ are independently selected from the group consisting of hydrogen, alkyl and haloalkyl; or $R_1$ and $R_5$ together with the ring to which they are attached form a 5-, 6- or 7-membered sulfur-containing ring with 1–2 double bonds and 0–2 oxo substituents; or A and $R_4$ together with the ring to which they are attached form a ring selected from the group consisting of a 5-, 6-, or 7-membered carbocyclic ring with 1–2 double bonds and 0–1 oxo substituents and a 5-, 6- or 7-membered sulfur-containing ring with 1–2 double bonds and 0–2 oxo substituents, provided that at least one of $R_1$ and $R_5$ or A and $R_4$ forms a ring.

DETAILED DESCRIPTION OF THE INVENTION

In one embodiment, the invention discloses a compound having Formula I

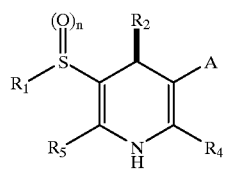

I or a pharmaceutically acceptable salt, ester, amide, or prodrug thereof ereof wherein $R_1$ is alkyl;

$R_2$ is selected from the group consisting of aryl and heteroaryl;

the aryl or heteroaryl can be optionally substituted;

n is 0–2;

A is selected from the group consisting of hydrogen, alkyl, and —X—$R_3$;

$R_3$ is alkyl or haloalkyl;

X is —C(O)— or —S(O)$_p$— wherein p is 1–2;

$R_4$ and $R_5$ are independently selected from the group consisting of hydrogen, alkyl and haloalkyl; or $R_1$ and $R_5$ together with the ring to which they are attached form a 5-, 6- or 7-membered sulfur-containing ring with 1–2 double bonds and 0–2 oxo substituents; or A and R₄ together with the ring to which they are attached form a ring selected from the group consisting of a 5-, 6-, or 7-membered carbocyclic ring with 1–2 double bonds and 0–1 oxo substituents and a 5-, 6- or 7-membered sulfur-containing ring with 1–2 double bonds and 0–2 oxo substituents, provided that at least one of $R_1$ and $R_5$ or A and $R_4$ forms a ring.

Another embodiment of the present invention includes a compound of formula II

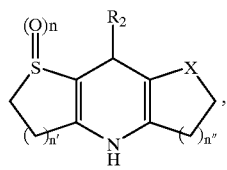

II or a pharmaceutically acceptable salt, ester, amide, or prodrug thereof, wherein $R_2$ is selected from the group consisting of aryl and heteroaryl;

the aryl or heteroaryl are optionally substituted;

n is 1 or 2;

X is selected from the group consisting of —CH₂—, —C(O)—, —S(O)—, or —S(O)₂—; and n' and n" are independently 1–3.

Another embodiment of the invention discloses pharmaceutical compositions containing compounds having the Formula I and II.

Yet another embodiment of the invention discloses methods of treatment comprising administering an effective amount of compounds having Formula I and II.

Definition of Terms

The term "alkanoyl" as used herein refers to an alkyl group appended to the parent molecular moiety through a carbonyl (—C(O)—) group. Examples of alkanoyl include acetyl, propionyl, and the like.

The term "alkanoyloxy" as used herein refers to an alkanoyl group attached to the parent molecular group through an oxygen atom.

The terms "loweralkyl" or "alkyl" as used herein refer to straight or branched chain alkyl radicals containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkenyl" as used herein refers to a monovalent group derived from a hydrocarbon containing at least one carbon-carbon double bond by the removal of a single hydrogen atom. Alkenyl groups include, for example, vinyl (ethenyl), allyl (propenyl), butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH₂CH=CH—, —C(CH₃)=CH—, —CH₂CH=CHCH₂—, and the like.

The term "alkylsulfinyl" as used herein refers to an alkyl group as previously defined appended to the parent molecular moiety through a sulfinyl (—S(O)) group. Examples of alkylsulfinyl include methylsulfinyl, ethylsulfinyl, isopropylsulfinyl and the like.

The term "alkylsulfonyl" as used herein refers to an alkyl group as previously defined appended to the parent molecular moiety through a sulfonyl (—S(O)₂) group. Examples of alkylsulfonyl include methylsulfonyl, ethylsulfonyl, isopropylsulfonyl and the like.

The term "alkynylene" refers to a divalent group derived by the removal of two hydrogen atoms from a straight or branched chain acyclic hydrocarbon group containing a carbon-carbon triple bond. Examples of alkynylene include —CC—, —CC—CH₂—, —CC—CH(CH₃)— and the like.

The term "alkoxy" as used herein refers to $R_{41}O$— wherein $R_{41}$ is a loweralkyl group, as defined above. Examples of alkoxy include, but are not limited to, ethoxy, tert-butoxy, and the like.

The term "alkoxyalkoxy" as used herein refers to an alkoxy group attached to the parent molecular group through another alkoxyl group. Examples of alkoxyalkoxy include ethoxymethoxy, propoxymethoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, isopropoxycarbonyl and the like.

The term "alkynyl" as used herein refers to a monovalent straight or branched chain group of 2 or more carbon atoms derived from at least one alkyne.

The term "aryl" as used herein refers to a mono- or bicyclic carbocyclic ring system having one or more aromatic rings including, but not limited to, phenyl, naphthyl, tetrahydronaphthyl, naphthyridinyl, indanyl, indenyl and the like. The aryl groups of this invention can be optionally substituted with 1–5 substituents independently selected from alkanoyl, alkenyl, alkoxy, alkoxyalkoxy, alkyl, alkylsulfinyl, alkylsulfonyl, alkoxycarbonyl, alkynyl, aryl, azido, carboxy, cyano, halo, haloalkyl, haloalkoxy, heteroaryl, hydroxy, nitro, thioalkoxy, —C(O)NR₆R₇ (wherein $R_6$ and $R_7$ are independently hydrogen, alkyl or aryl), thioureido, ureido, and —S(O)ₚNR₆R₇. In addition, substituted aryl groups include tetrafluorophenyl and pentafluorophenyl.

The term "arylalkyl" as used herein refers to an aryl group as previously defined, appended to a loweralkyl radical, for example, benzyl and the like.

The term "azido" as defined herein refers to —N₃.

The term "carboxy" as used herein refers to —CO₂H.

The term "cyano" as used herein refers to —CN.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "halogen" or "halo" as used herein refers to I, Br, Cl or F.

The term "haloalkyl" as used herein refers to a lower alkyl radical, as defined above, bearing at least one halogen substituent, for example, chloromethyl, fluoroethyl, 1-chloro-2-fluoropropyl, 2,3-dichoropropyl, or trifluoroethyl and the like.

The term "haloalkoxy" as used herein refers to a lower alkoxyl radical, as defined above, bearing at least one halogen substituent, for example, chloromethoxy, fluoroethoxy, 1-chloro-2-fluoropropoxy, 2,3-dichoropropoxy, or trifluoroethoxy and the like.

The term "heteroaryl" as used herein represents an aromatic 5-, 6- or 7-membered ring containing one, two or three heteroatoms independently selected from the group consisting of nitrogen, oxygen and sulfur. The 5-membered ring has two double bonds and the 6- and 7-membered rings have three double bonds. The term "heteroaryl" also includes bicyclic, tricyclic and tetracyclic groups in which any of the above heteroaryl rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. The heteroaryl groups of this invention can be optionally substituted with 1–4 substituents independently selected from alkanoyl, alkenyl, alkoxy, alkyl, alkylsulfinyl, alkylsulfonyl, alkoxycarbonyl, alkynyl, aryl, azido, carboxy, cyano, halo, haloalkyl, haloalkoxy, heteroaryl, hydroxy, hydroxyalkyl, nitro, thioalkoxy, —C(O)NR$_6$R$_7$ (wherein R$_6$ and R$_7$ are independently hydrogen, alkyl or aryl), thioureido, ureido, and —S(O)$_p$NR$_6$R$_7$. Examples of heteroaryl include, but are not limited to, indolyl, quinolyl, isoquinolyl, tetrahydroquinolyl, benzofuryl, benzothienyl, pyrrolyl, pyrazolyl, imidazolyl, pyridyl, pyrazinyl, pyrimidinyl, pyridazinyl, oxazolyl, isoxazolyl, thiazolyl, isothiazolyl, benzimidazolyl, benzothiazolyl, benzoxazolyl, furyl, thienyl, benzoxadiazole, and benzothiadiazole.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. "Heteroaryl" as defined above is a subset of "heterocyclic" The nitrogen heteroatoms can be optionally quaternized. The term "heterocyclic" also includes bicyclic groups in which any of the above heterocyclic rings is fused to a cyclohexane ring or another heterocyclic ring (for example and the like). Heterocyclics include: azetidinyl, pyrrolinyl, pyrrolidinyl, pyrazolinyl, pyrazolidinyl, imidazolinyl, imidazolidinyl, piperidinyl, homopiperidinyl, piperazinyl, oxazolidinyl, isoxazolidinyl, morpholinyl, thiazolidinyl, isothiazolidinyl, indolyl, quinolinyl, isoquinolinyl and the like.

Heterocyclics can be unsubstituted or mono-, di-, or trisubstituted with substituents independently selected from hydroxy, halo, oxo (═O), alkylamino (R*N═ wherein R* is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "hydroxy" as used herein refers to —OH.

The term "hydroxyalkyl" as used herein refers to a lower alkyl radical, as defined above, bearing at least one hydroxy substituent, for example, hydroxymethyl, hydroxyethyl, 1-hydroxy-2-hydroxypropyl, 2,3-dihydroxypropyl, and the like.

The term "nitro" as used herein refers to —NO$_2$.

The term "thioalkoxy" as used herein refers to R$_{70}$S— wherein R$_{70}$ is loweralkyl. Examples of thioalkoxy include, but are not limited to, methylthio, ethylthio and the like.

The term "thioureido" as used herein refers to —NH—SC—NH$_2$.

The term "ureido" as used herein refers to —NH—CO—NH$_2$.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood, and include esters and amide analogs of the compounds of the present invention. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Representative compounds of the present invention include, but are not intended to be limited to:

3,4,6,7,8,10-hexahydro-10-phenyl-2H-thiopyrano[3,2-b]quinolin-9(5H)-one, 1,1-dioxide, 3,4,6,7,8,10-hexahydro-10-(3-nitrophenyl)-2H-thiopyrano[3,2-b]quinolin-9(5H)-one, 1,1-dioxide, 10-(3-cyanophenyl)-3,4,6,7,8,10-hexahydro-2H-thiopyrano[3,2-b]quinolin-9(5H)-one, 1,1-dioxide, 3,4,6,7,8,10-hexahydro-10-[3-(trifluoromethyl)phenyl]-2H-thiopyrano[3,2-b]quinolin-9(5H)-one, 1,1-dioxide, 10-(3-bromophenyl)-3,4,6,7,8,10-hexahydro-2H-thiopyrano[3,2-b]quinolin-9(5H)-one, 1,1-dioxide, 10-(3-fluorophenyl)-3,4,6,7,8,10-hexahydro-2H-thiopyrano[3,2-b]quinolin-9(5H)-one, 1,1-dioxide, 10-(3-chlorophenyl)-3,4,6,7,8,10-hexahydro-2H-thiopyrano[3,2-b]quinolin-9(5H)-one, 1,1-dioxide, 3,4,6,7,8,10-hexahydro-10-[4-(trifluoromethyl)phenyl]-2H-thiopyrano[3,2-b]quinolin-9(5H)-one, 1,1-dioxide, 10-(4-bromophenyl)-3,4,6,7,8,10-hexahydro-2H-thiopyrano[3,2-b]quinolin-9(5H)-one, 1,1-dioxide,
10-(3,4-dichlorophenyl)-3,4,6,7,8,10-hexahydro-2H-thiopyrano[3,2-b]quinolin-9(5H)-one, 1,1-dioxide,
10-(3-chloro-4-fluorophenyl)-3,4,6,7,8,10-hexahydro-2H-thiopyrano[3,2-b]quinolin-9(5H)-one, 1,1-dioxide,
10-(3-bromo-4-fluorophenyl)-3,4,6,7,8,10-hexahydro-2H-thiopyrano[3,2-b]quinolin-9(5H)-one, 1,1-dioxide,
10-(3,4-difluorophenyl)-3,4,6,7,8,10-hexahydro-2H-thiopyrano[3,2-b]quinolin-9(5H)-one, 1,1-dioxide,
10-[3-fluoro-5-(trifluoromethyl)phenyl]-3,4,6,7,8,10-hexahydro-2H-thiopyrano[3,2-b]quinolin-9(5H)-one, 1,1-dioxide,
10-[4-fluoro-3-(trifluoromethyl)phenyl]-3,4,6,7,8,10-hexahydro-2H-thiopyrano[3,2-b]quinolin-9(5H)-one, 1,1-dioxide,
3,4,6,7,8,10-hexahydro-10-(4-methyl-3-nitrophenyl)2H-thiopyrano[3,2-b]quinolin-9(5H)-one, 1,1-dioxide,
10-(4-chloro-3-fluorophenyl)-3,4,6,7,8,10-hexahydro-2H-thiopyrano[3,2-b]quinolin-9(5H)-one, 1,1-dioxide,
10-(4-chloro-3-nitrophenyl)-3,4,6,7,8,10-hexahydro-2H-thiopyrano[3,2-b]quinolin-9(5H)-one, 1,1-dioxide;
3,4,6,7,8,10-hexahydro-10-(3,4,5-trifluorophenyl)-2H-thiopyrano[3,2-b]quinolin-9(5H)-one, 1,1-dioxide;
10-(3-pyridyl)-3,4,6,7,8,10-hexahydro-2H-thiopyrano[3,2-b]quinolin-9(5H)-one, 1,1-dioxide;
10-(4-pyridyl)-3,4,6,7,8,10-hexahydro-2H-thiopyrano[3,2-b]quinolin-9(5H)-one, 1,1-dioxide;
9-(3-cyanophenyl)-3,4,5,6,7,9-hexahydrothieno[3,2-b]quinolin-8(2H)-one, 1,1-dioxide;
9-(3-nitrophenyl)-3,4,5,6,7,9-hexahydrothieno[3,2-b]quinolin-8(2H)-one, 1,1-dioxide;
9-(3,4-dichlorophenyl)-3,4,5,6,7,9-hexahydrothieno[3,2-b]quinolin-8(2H)-one, 1,1-dioxide;
9-[4-fluoro-3-(trifluoromethyl)phenyl]-3,4,5,6,7,9-hexahydrothieno[3,2-b]quinolin-8(2H)-one, 1,1-dioxide;
3,4,5,6,7,9-hexahydro-9-(4-methyl-3-nitrophenyl)thieno[3,2-b]quinolin-8(2H)-one, 1,1-dioxide;
9-(3,4-difluorophenyl)-3,4,5,6,7,9-hexahydrothieno[3,2-b]quinolin-8(2H)-one, 1,1-dioxide;
9-(4-chloro-3-nitrophenyl)-3,4,5,6,7,9-hexahydrothieno[3,2-b]quinolin-8(2H)-one, 1,1-dioxide;
9-(3-bromo-4-fluorophenyl)-3,4,5,6,7,9-hexahydrothieno[3,2-b]quinolin-8(2H)-one, 1,1-dioxide;
4-(3-cyanophenyl)-4,6,7,8-tetrahydro-2-methyl-3-(methylsulfonyl)-5(1H)-quinolinone;
4,6,7,8-tetrahydro-2-methyl-3-(methylsulfonyl)-4-(3-nitrophenyl)-5(1H)-quinolinone;
4,6,7,8-tetrahydro-2-methyl-3-(methylsulfonyl)-4-[4-(trifluoromethyl)phenyl]-5(1H)-quinolinone;
4-(3,4-dichlorophenyl)-4,6,7,8-tetrahydro-2-methyl-3-(methylsulfonyl)-5(1H)-quinolinone;
4,6,7,8-tetrahydro-2-methyl-4-(4-methyl-3-nitrophenyl)-3-(methylsulfonyl)-5(1H)-quinolinone;
4-(4-chloro-3-nitrophenyl)-4,6,7,8-tetrahydro-2-methyl-3-(methylsulfonyl)-5(1H)-quinolinone;
4-(3-bromo-4-fluorophenyl)-4,6,7,8-tetrahydro-2-methyl-3-(methylsulfonyl)-5(1H)-quinolinone;
4-(4-chloro-3-fluorophenyl)-4,6,7,8-tetrahydro-2-methyl-3-(methylsulfonyl)-5(1H)-quinolinone;
4-(3,4,5-trifluorophenyl)-4,6,7,8-tetrahydro-2-methyl-3-(methylsulfonyl)-5(1H)-quinolinone;
9-(3-cyano)-3,4,5,6,7,9-hexahydrocyclopenta[b]thiopyrano[2,3-e]pyridin-8(2H)-one, 1,1-dioxide;
9-(3,4-dichlorophenyl)-3,4,5,6,7,9-hexahydrocyclopenta[b]thio-pyrano[2,3-e]pyridin-8(2H)-one, 1,1-dioxide;
9-(4-chloro-3-nitrophenyl)-3,4,5,6,7,9-hexahydrocyclopenta[b]thiopyrano[2,3-e]pyridin-8(2H)-one, 1,1-dioxide;
9-(3-chloro-4-fluorophenyl)-3,4,5,6,7,9-hexahydrocyclopenta[b]thiopyrano[2,3-e]pyridin-8(2H)-one, 1,1-dioxide;
9-(3-bromo-4-fluorophenyl)-3,4,5,6,7,9-hexahydrocyclopenta[b]thiopyrano[2,3-e]pyridin-8(2H)-one, 1,1-dioxide;
9-(4-fluoro-3-trifluoromethyl)-3,4,5,6,7,9-hexahydrocyclopenta[b]-thiopyrano [2,3-e]pyridin-8(2H)-one, 1,1-dioxide;
9-(4-methyl-3-nitro)-3,4,5,6,7,9-hexahydrocyclopenta[b]thio-pyrano[2,3-e]pyridin-8(2H)-one, 1,1-dioxide;
8-(4-chloro-3-nitrophenyl)-3,5,6,8-tetrahydro-2H-cyclopenta[b]thieno[2,3-e]pyridin-7(4H)-one, 1,1-dioxide;
8-(3-bromo-4-fluorophenyl)-3,5,6,8-tetrahydro-2H-cyclopenta[b]thieno[2,3-e]pyridin-7(4H)-one, 1,1-dioxide;
1-[8-(3,4-dichlorophenyl)-3,4,5,8-tetrahydro-6-methyl-1,1-dioxido-2H-thiopyrano[3,2-b]pyridin-7-yl]ethanone;
1-[8-(4-chloro-3-nitrophenyl)-3,4,5,8-tetrahydro-6-methyl-1,1-dioxido-2H-thiopyrano[3,2-b]pyridin-7-yl]ethanone;
10-(4-chloro-3-nitrophenyl)-3,4,6,7,10-hexahydro-2H,5H-bisthiopyrano[3,2-b:2',3'-e]pyridine, 1,1,9,9-tetraoxide;
3,4,6,7,8,10-hexahydro-10-phenyl-2H-thiopyrano[3,2-b]quinolin-9(5H)-one, 1,1-dioxide;
3,4,6,7,8,10-hexahydro-10-(3-nitrophenyl)-2H-thiopyrano[3,2-b]quinolin-9(5H)-one, 1,1-dioxide;
10-(3-cyanophenyl)-3,4,6,7,8,10-hexahydro-2H-thiopyrano[3,2-b]quinolin-9(5H)-one, 1,1-dioxide;
3,4,6,7,8,10-hexahydro-10-[3-(trifluoromethyl)phenyl]-2H-thiopyrano[3,2-b]quinolin-9(5H)-one, 1,1-dioxide;
10-(3-bromophenyl)-3,4,6,7,8,10-hexahydro-2H-thiopyrano[3,2-b]quinolin-9(5H)-one, 1,1-dioxide;
10-(3-fluorophenyl)-3,4,6,7,8,10-hexahydro-2H-thiopyrano[3,2-b]quinolin-9(5H)-one, 1,1-dioxide;
10-(3-chlorophenyl)-3,4,6,7,8,10-hexahydro-2H-thiopyrano[3,2-b]quinolin-9(5H)-one, 1,1-dioxide;
3,4,6,7,8,10-hexahydro-10-[4-(trifluoromethyl)phenyl]-2H-thiopyrano[3,2-b]quinolin-9(5H)-one, 1,1-dioxide;
10-(4-bromophenyl)-3,4,6,7,8,10-hexahydro-2H-thiopyrano[3,2-b]quinolin-9(5H)-one, 1,1-dioxide;
10-(3,4-dichlorophenyl)-3,4,6,7,8,10-hexahydro-2H-thiopyrano[3,2-b]quinolin-9(5H)-one, 1,1-dioxide;
10-(3-chloro-4-fluorophenyl)-3,4,6,7,8,10-hexahydro-2H-thiopyrano[3,2-b]quinolin-9(5H)-one, 1,1-dioxide;
10-(3-bromo-4-fluorophenyl)-3,4,6,7,8,10-hexahydro-2H-thiopyrano[3,2-b]quinolin-9(5H)-one, 1,1-dioxide;
10-(3,4-difluorophenyl)-3,4,6,7,8,10-hexahydro-2H-thiopyrano[3,2-b]quinolin-9(5H)-one, 1,1-dioxide;
10-[3-fluoro-5-(trifluoromethyl)phenyl]-3,4,6,7,8,10-hexahydro-2H-thiopyrano[3,2-b]quinolin-9(5H)-one, 1,1-dioxide;
10-[4-fluoro-3-(trifluoromethyl)phenyl]-3,4,6,7,8,10-hexahydro-2H-thiopyrano[3,2-b]quinolin-9(5H)-one, 1,1-dioxide;

3,4,6,7,8,10-hexahydro-10-(4-methyl-3-nitrophenyl)2H-thiopyrano[3,2-b]quinolin-9(5H)-one, 1,1-dioxide;

10-(4-chloro-3-fluorophenyl)-3,4,6,7,8,10-hexahydro-2H-thiopyrano[3,2-b]quinolin-9(5H)-one, 1,1-dioxide;

10-(4-chloro-3-nitrophenyl)-3,4,6,7,8,10-hexahydro-2H-thiopyrano[3,2-b]quinolin-9(5H)-one, 1,1-dioxide;

3,4,6,7,8,10-hexahydro-10-(3,4,5-trifluorophenyl)-2H-thiopyrano[3,2-b]quinolin-9(5H)-one, 1,1-dioxide;

10-(3-pyridyl)-3,4,6,7,8,10-hexahydro-2H-thiopyrano[3,2-b]quinolin-9(5H)-one, 1,1-dioxide;

10-(4-pyridyl)-3,4,6,7,8,10-hexahydro-2H-thiopyrano[3,2-b]quinolin-9(5H)-one, 1,1-dioxide;

9-(3-cyanophenyl)-3,4,5,6,7,9-hexahydrothieno[3,2-b]quinolin-8(2H)-one, 1,1-dioxide;

9-(3-nitrophenyl)-3,4,5,6,7,9-hexahydrothieno[3,2-b]quinolin-8(2H)-one, 1,1-dioxide;

9-(3,4-dichlorophenyl)-3,4,5,6,7,9-hexahydrothieno[3,2-b]quinolin-8(2H)-one, 1,1-dioxide;

9-[4-fluoro-3-(trifluoromethyl)phenyl]-3,4,5,6,7,9-hexahydrothieno[3,2-b]quinolin-8(2H)-one, 1,1-dioxide;

3,4,5,6,7,9-hexahydro-9-(4-methyl-3-nitrophenyl)thieno[3,2-b]quinolin-8(2H)-one, 1,1-dioxide;

9-(3,4-difluorophenyl)-3,4,5,6,7,9-hexahydrothieno[3,2-b]quinolin-8(2H)-one, 1,1-dioxide;

9-(4-chloro-3-nitrophenyl)-3,4,5,6,7,9-hexahydrothieno[3,2-b]quinolin-8(2H)-one, 1,1-dioxide;

9-(3-bromo-4-fluorophenyl)-3,4,5,6,7,9-hexahydrothieno[3,2-b]quinolin-8(2H)-one, 1,1-dioxide;

4-(3-cyanophenyl)-4,6,7,8-tetrahydro-2-methyl-3-(methylsulfonyl)-5(1H)-quinolinone;

4,6,7,8-tetrahydro-2-methyl-3-(methylsulfonyl)-4-(3-nitrophenyl)-5(1H)-quinolinone;

4,6,7,8-tetrahydro-2-methyl-3-(methylsulfonyl)-4-[4-(trifluoromethyl)phenyl]-5(1H)-quinolinone;

4-(3,4-dichlorophenyl)-4,6,7,8-tetrahydro-2-methyl-3-(methylsulfonyl)-5(1H)-quinolinone;

4,6,7,8-tetrahydro-2-methyl-4-(4-methyl-3-nitrophenyl)-3-(methylsulfonyl)-5(1H)-quinolinone;

4-(4-chloro-3-nitrophenyl)-4,6,7,8-tetrahydro-2-methyl-3-(methylsulfonyl)-5(1H)-quinolinone;

4-(3-bromo-4-fluorophenyl)-4,6,7,8-tetrahydro-2-methyl-3-(methylsulfonyl)-5(1H)-quinolinone;

4-(4-chloro-3-fluorophenyl)-4,6,7,8-tetrahydro-2-methyl-3-(methylsulfonyl)-5(1H)-quinolinone;

4-(3,4,5-trifluorophenyl)-4,6,7,8-tetrahydro-2-methyl-3-(methylsulfonyl)-5(1H)-quinolinone;

9-(3-cyano)-3,4,5,6,7,9-hexahydrocyclopenta[b]thiopyrano[2,3-e]pyridin-8(2H)-one, 1,1-dioxide;

9-(3,4-dichlorophenyl)-3,4,5,6,7,9-hexahydrocyclopenta[b]thio-pyrano[2,3-e]pyridin-8(2H)-one, 1,1-dioxide;

9-(4-chloro-3-nitrophenyl)-3,4,5,6,7,9-hexahydrocyclopenta[b]thiopyrano[2,3-e]pyridin-8(2H)-one, 1,1-dioxide;

9-(3-chloro-4-fluorophenyl)-3,4,5,6,7,9-hexahydrocyclopenta[b]thiopyrano[2,3-e]pyridin-8(2H)-one, 1,1-dioxide;

9-(3-bromo-4-fluorophenyl)-3,4,5,6,7,9-hexahydrocyclopenta[b]thiopyrano[2,3-e]pyridin-8(2H)-one, 1,1-dioxide;

9-(4-fluoro-3-trifluoromethyl)-3,4,5,6,7,9-hexahydrocyclopenta[b]-thiopyrano[2,3-e]pyridin-8(2H)-one, 1,1-dioxide;

9-(4-methyl-3-nitro)-3,4,5,6,7,9-hexahydrocyclopenta[b]thio-pyrano[2,3-e]pyridin-8(2H)-one, 1,1-dioxide;

8-(4-chloro-3-nitrophenyl)-3,5,6,8-tetrahydro-2H-cyclopenta[b]thieno[2,3-e]pyridin-7(4H)-one, 1,1-dioxide;

8-(3-bromo-4-fluorophenyl)-3,5,6,8-tetrahydro-2H-cyclopenta[b]thieno[2,3-e]pyridin-7(4H)-one, 1,1-dioxide;

1-[8-(3,4-dichlorophenyl)-3,4,5,8-tetrahydro-6-methyl-1,1-dioxido-2H-thiopyrano[3,2-b]pyridin-7-yl]ethanone;

1-[8-(4-chloro-3-nitrophenyl)-3,4,5,8-tetrahydro-6-methyl-1,1-dioxido-2H-thiopyrano[3,2-b]pyridin-7-yl]ethanone;

10-(4-chloro-3-nitrophenyl)-3,4,6,7,10-hexahydro-2H,5H-bisthiopyrano[3,2-b:2',3'-e]pyridine, 1,1,9,9-tetraoxide;

9-(3,4-Difluorophenyl)-3,4,5,6,7,9-hexahydrocyclopenta[b]thiopyrano[2,3-e]pyridin-8(2H)-one, 1,1-dioxide;

8-(4-Chloro-3-nitrophenyl)-2,3,4,5,6,8-hexahydrothieno[3,2-b:2i,3i-e]pyridine, 1,1,7,7-tetraoxide;

8-(3-Cyanophenyl)-2,3,4,5,6,8-hexahydro-7H-cyclopenta[b]thieno[2,3-e]pyridin-7-one, 1,1-dioxide;

8-(3-Bromo-4-fluorophenyl)-2,3,4,5,6,8-hexahydrothieno[3,2-b:2i,3i-e]pyridine, 1,1,7,7-tetraoxide;

10-(3-Bromo-4-fluorophenyl)-3,4,6,7,8,10-hexahydro-2H,5H-dithiopyrano[3,2-b:2i,3i-e]pyridine, 1,1,9,9-tetraoxide;

3,4,5,6,7,9-Hexahydro-9-(3-nitrophenyl)cyclopenta[b]thiopyrano[2,3-e]pyridin-8(2H)-one, 1,1-dioxide;

8-(3-Bromo-4-fluorophenyl)-2,3,4,5,6,8-hexahydro-7H-cyclopenta[b]thieno[2,3-e]pyridin-7-one, 1,1-dioxide;

8-(4-fluoro-3-trifluoromethylphenyl)-2,3,4,5,6,8-hexahydro-7H-cyclopenta[b]thieno[2,3-e]pyridin-7-one, 1,1-dioxide;

2,3,4,5,6,8-Hexahydro-8-(3-nitrophenyl)-7H-cyclopenta[b]thieno[2,3-e]pyridin-7-one, 1,1-dioxide;

3,4,6,7,8,10-Hexahydro-10-(3-nitrophenyl)-2H,5H-dithiopyrano[3,2-b:2i,3i-e]pyridine, 1,1,9,9-tetraoxide;

8-(3,4-Dichlorophenyl)-2,3,4,5,6,8-hexahydro-7H-cyclopenta[b]thieno[2,3-e]pyridin-7-one, 1,1-dioxide;

8-(3-Chloro-4-fluorophenyl)-2,3,4,5,6,8-hexahydro-7H-cyclopenta[b]thieno[2,3-e]pyridin-7-one, 1,1-dioxide;

8-(3-Cyanophenyl)-2,3,4,5,6,8-hexahydrothieno[3,2-b:2i,3i-e]pyridine, 1,1,7,7-tetraoxide;

8-(2-Cyano-4-pyridinyl)-2,3,4,5,6,8-hexahydro-7H-cyclopenta[b]thieno[2,3-e]pyridin-7-one, 1,1-dioxide;

8-(3-Bromophenyl)-2,3,4,5,6,8-hexahydro-7H-cyclopenta[b]thieno[2,3-e]pyridin-7-one, 1,1-dioxide;

8-(4-Fluoro-3-trifluoromethylphenyl)-2,3,4,5,6,8-hexahydrothieno[3,2-b:2i,3i-e]pyridine, 1,1,7,7-tetraoxide;

8-(4-Bromo-2-thienyl)-2,3,4,5,6,8-hexahydro-7H-cyclopenta[b]thieno[2,3-e]pyridin-7-one, 1,1-dioxide;

8-(5-Bromo-2-thienyl)-2,3,4,5,6,8-hexahydro-7H-cyclopenta[b]thieno[2,3-e]pyridin-7-one, 1,1-dioxide;

2,3,4,5,6,8-Hexahydro-8-(5-nitro-3-thienyl)-7H-cyclopenta[b]thieno[2,3-e]pyridin-7-one, 1,1-dioxide;

2,3,4,5,6,8-Hexahydro-8-(5-nitro-2-thienyl)-7H-cyclopenta[b]thieno[2,3-e]pyridin-7-one, 1,1-dioxide;

2,3,4,5,6,8-Hexahydro-8-(5-nitro-2-furyl)-7H-cyclopenta[b]thieno[2,3-e]pyridin-7-one, 1,1-dioxide;

8-(3,4-Dibromophenyl)-2,3,4,5,6,8-hexahydro-7H-cyclopenta[b]thieno[2,3-e]pyridin-7-one, 1,1-dioxide;

2,3,4,5,6,8-Hexahydro-8-(3-nitrophenyl)dithieno[3,2-b:2i,3i-e]pyridine, 1,1,7,7-tetraoxide;
8-(3-Chloro-4-fluorophenyl)-2,3,4,5,6,8-hexahydrothieno[3,2-b:2i,3i-e]pyridine, 1,1,7,7-tetraoxide;
8-(3,4-Chlorophenyl)-2,3,4,5,6,8-hexahydrothieno[3,2-b:2i,3i-e]pyridine, 1,1,7,7-tetraoxide;
8-(4-Bromophenyl)-2,3,4,5,6,8-hexahydro-7H-cyclopenta[b]thieno[2,3-e]pyridin-7-one, 1,1-dioxide;
8-(3,4-Difluorophenyl)-2,3,4,5,6,8-hexahydro-7H-cyclopenta[b]thieno[2,3-e]pyridin-7-one, 1,1-dioxide;
8-(4-Chloro-3-fluorophenyl)-2,3,4,5,6,8-hexahydro-7H-cyclopenta[b]thieno[2,3-e]pyridin-7-one, 1,1-dioxide;
9-(3-Chloro-4-fluorophenyl)-2,3,5,6,7,9-hexahydrothieno[3,2-b]quinolin-8(4H)-one, 1,1-dioxide;
8-(3-Cyano-4-fluorophenyl)-2,3,4,5,6,8-hexahydrothieno[3,2-b:2i,3i-e]pyridine, 1,1,7,7-tetraoxide;
(+)(9R)-9-(3-Bromo-4-fluorophenyl)-2,3,5,6,7,9-hexahydrothieno[3,2-b]quinolin-8(4H)-one, 1,1-dioxide;
(−)(9S)-9-(3-Bromo-4-fluorophenyl)-2,3,5,6,7,9-hexahydrothieno[3,2-b]quinolin-8(4H)-one, 1,1-dioxide;
8-(2,1,3-Benzoxadiazol-5-yl)-2,3,4,5,6,8-hexahydro-7H-cyclopenta[b]thieno[2,3-e]pyridin-7-one, 1,1-dioxide;
(−)(8S)-8-(3-Bromo-4-fluorophenyl)-2,3,4,5,6,8-hexahydro-7H-cyclopenta[b]thieno[2,3-e]pyridin-7-one, 1,1-dioxide;
(+)(8R)-8-(3-Bromo-4-fluorophenyl)-2,3,4,5,6,8-hexahydro-7H-cyclopenta[b]thieno[2,3-e]pyridin-7-one, 1,1-dioxide;
9-(2,1,3-Benzoxadiazol-5-yl)-2,3,5,6,7,9-hexahydrothieno[3,2-b]quinolin-8(4H)-one, 1,1-dioxide;
9-(4-Fluoro-3-iodophenyl)-2,3,5,6,7,9-hexahydrothieno[3,2-b]quinolin-8(4H)-one, 1,1-dioxide;
8-(4-Fluoro-3-iodophenyl)-2,3,4,5,6,8-hexahydro-7H-cyclopenta[b]thieno[2,3-e]pyridin-7-one, 1,1-dioxide;
(+)9-(3-Bromo-4-fluorophenyl)-3,4,5,6,7,9-hexahydrocyclopenta[b]thiopyrano[2,3-e]pyridin-8(2H)-one, 1,1-dioxide;
(−)9-(3-Bromo-4-fluorophenyl)-3,4,5,6,7,9-hexahydrocyclopenta[b]thiopyrano[2,3-e]pyridin-8(2H)-one, 1,1-dioxide;
(+)10-(3-Bromo-4-fluorophenyl)-3,4,6,7,8,10-hexahydro-2H-thiopyrano[3,2-b]quinolin-9(5H)-one, 1,1-dioxide;
(−)10-(3-Bromo-4-fluorophenyl)-3,4,6,7,8,10-hexahydro-2H-thiopyrano[3,2-b]quinolin-9(5H)-one, 1,1-dioxide;
(+)(9R)-9-(3,4-Dichlorophenyl)-3,4,5,6,7,9-hexahydrothieno[3,2-b]quinolin-8(2H)-one, 1,1-dioxide;
(−)(9S)-9-(3,4-Dichlorophenyl)-3,4,5,6,7,9-hexahydrothieno[3,2-b]quinolin-8(2H)-one, 1,1-dioxide;
(+)(9R)-9-(2,1,3-Benzoxadiazol-5-yl)-2,3,5,6,7,9-hexahydrothieno[3,2-b]quinolin-8(4H)-one, 1,1-dioxide;
(−)(9S)-9-(2,1,3-Benzoxadiazol-5-yl)-2,3,5,6,7,9-hexahydrothieno[3,2-b]quinolin-8(4H)-one, 1,1-dioxide;
(+)(9R)-9-(4-chloro-3-nitrophenyl)-3,4,5,6,7,9-hexahydrothieno[3,2-b]quinolin-8(2H)-one, 1,1-dioxide;
(−)(9S)-9-(4-chloro-3-nitrophenyl)-3,4,5,6,7,9-hexahydrothieno[3,2-b]quinolin-8(2H)-one, 1,1-dioxide;
11-(3-Bromo-4-fluorophenyl)-2,3,4,5,7,8,9,11-octahydrothiepino[3,2-b]quinolin-10(6H)-one, 1,1-dioxide; and
10-(3-Bromo-4-fluorophenyl)-2,3,4,5,6,7,8,10-octahydro-9H-cyclopenta[b]thiepino[2,3-e]pyridin-9-one, or a pharmaceutically acceptable salt, ester, amide or prodrug thereof.

Preparation of Compounds of The Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–2.

Scheme 1

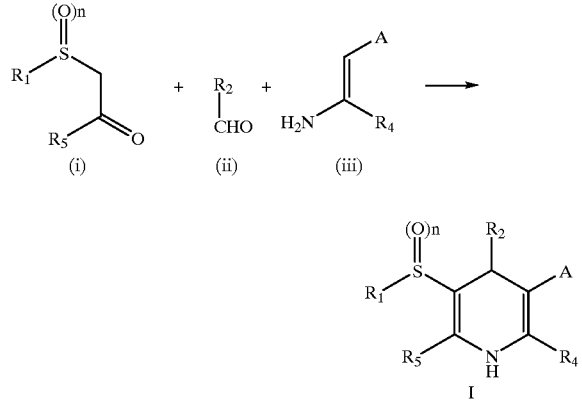

As shown in Scheme 1, the dihydropyridines of Formula I were prepared by heating ketone (i) with aldehyde (ii) and enamine (iii) in a protic solvent such as ethyl alcohol. For the case where $R_1$ and $R_5$ form a 5-membered ring, an additional heating step can be required to provide the product.

Scheme 2

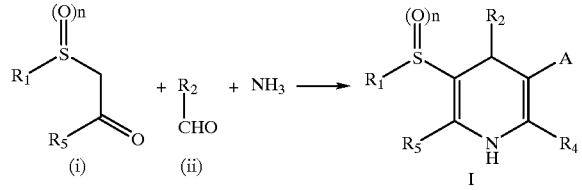

As shown in Scheme 2, for those examples wherein X is $S(O)_p$ wherein p is 2, $R_1=R_3$, and $R_4=R_5$, dihydropyridines of Formula I were prepared by heating 2 equivalents of (i) with 1 equivalent of (ii) and concentrated ammonium hydroxide in a protic solvent such as ethyl alcohol.

The following methods are intended as an illustration of and not a limitation upon the scope of the invention as defined in the appended claims. Further, all citations herein are incorporated by reference.

Scheme 3

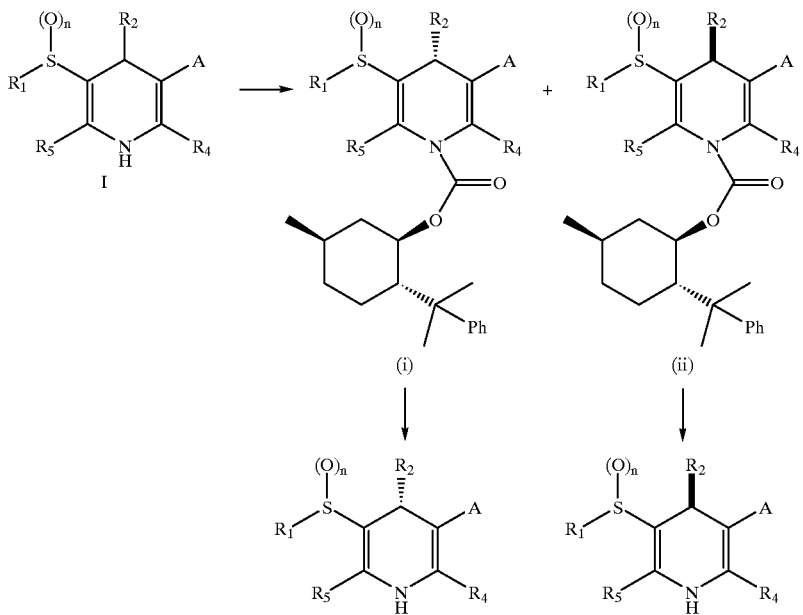

Examples of the present Invention that possess a center of chirality and thus exist in racemic form were separated into the individual enantiomers by the method shown in Scheme 3. The racemic compounds of general formula I were reacted with potassium t-butoxide (1 equivalent) in tetrahydrofuran followed by 8-phenylmenthyl chloroformate to generate a mixture of diastereomeric 8-phenylmenthyl carbamates (i) and (ii). The diastereomers (i) and (ii) were separated by column chromatography over silica gel and the 8-phenylmenthol moiety removed by reaction with sodium methoxide in methanol to provide the single enantiomers as shown.

In addition to the use of the method illustrated in Scheme 3, individual enantiomers of compounds of the Invention were also separated by chiral chromatography.

EXAMPLE 1

3,4,6,7,8,10-hexahydro-10-(3-nitrophenyl)-2H-thiopyrano[3,2-b]quinolin-9(5H)-one 1,1-dioxide A solution of 3-nitrobenzaldehyde (151 mg, 1.00 mmol), tetrahydrothiopyran-3-one-1,1-dioxide (148 mg, 1.00 mmol), prepared according to the method described in J. Heterocycl. Chem. (1990), 27, 1453, and 3-amino-2-cyclohexen-1-one (111 mg, 1.00 mmol) in ethanol (7 mL) was heated at reflux for 24 hours and cooled. The solid that precipitated was washed with ethanol, dried, and triturated with hot methanol to provide the title compound. MS (APCI) m/e 375 (M+H)$^+$; $^1$H NMR (DMSO-d$_6$) 1.75 (m, 1H), 1.90 (m, 1H), 2.22 (m, 4H), 2.55 (m, 4H), 3.22 (m, 2H), 5.15 (s, 1H), 7.55 (t, 1H), 765 (d, 1H), 8.00 (m, 1H), 9.48 (br s, 1H); Anal. Calcd for C, 57.74; H, 4.85; N, 7.48. Found: C, 57.41; H, 4.75; N, 7.39.

EXAMPLE 2

10-(3,4-dichlorophenyl)-3,4,6,7,8,10-hexahydro-2H-thiopyrano[3,2-b]quinolin-9(5H)-one, 1.1-dioxide 3,4-Dichlorobenzaldehyde (175 mg, 1.00 mmol) was processed as in Example 1 to provide the title compound. MS (APCI) m/e 398 (M+H)$^+$, 400 (M+H)$^+$; $^1$H NMR (DMSO-d$_6$) 1.75 (m, 1H), 1.90 (m, 1H), 2.22 (m, 4H), 2.55 (m, 4H), 3.20 (m, 2H), 5.01 (s, 1H), 7.06 (dd, 1H), 7.32 (d, 1H), 7.50 (d, 1H), 9.40 (br s, 1H); Anal. Calcd for C$_{18}$H$_{17}$Cl$_2$NO$_3$S: C, 54.28; H, 4.30; N, 3.52. Found: C, 54.13; H, 4.18; N, 3.46.

EXAMPLE 3

10-(3-chloro-4-fluorophenyl)-3,4,6,7,8,10-hexahydro-2H-thiopyrano[3,2-b]quinolin-9(5H)-one, 1.1-dioxide 3-Chloro-4-fluorobenzaldehyde (159 mg, 1.00 mmol) was processed as in Example 1 to provide the title compound. MS (APCI) m/e 382 (M+H)$^+$, 384 (M+H)$^+$; $^1$H NMR (DMSO-d$_6$) 1.75 (m, 1H), 1.88 (m, 1H), 2.20 (m, 4H), 2.50 (m, 4H), 3.20 (m, 2H), 5.01 (s, 1H), 7.15 (ddd, 1H), 7.26 (m, 3H), 9.38 (br s, 1H); Anal. Calcd for C$_{18}$H$_{17}$ClFNO$_3$S: C, 56.62; H, 4.49; N, 3.67. Found: C, 56.64; H, 4.43; N, 3.57.

EXAMPLE 4

10-(3-bromo-4-fluorophenyl)-3,4,6,7,8,10-hexahydro-2H-thiopyrano[3,2-b]quinolin-9(5H)-one 1,1-dioxide 3-Bromo-4-fluorobenzaldehyde (203 mg, 1.00 mmol) was processed as in Example 1 to provide the title compound. MS (APCI) m/e 426 (M+H)$^+$, 428 (M+H)$^+$; $^1$H NMR (DMSO-d$_6$) 1.75 (m, 1H), 1.90 (m, 1H), 2.20 (m, 4H), 2.55 (m, 4H), 3.20 (m, 2H), 5.01 (s, 1H), 7.20 (m, 2H), 7.40 (dd, 1H), 9.35 (br s, 1H); Anal. Calcd for C$_{18}$H$_{17}$BrFNO$_3$S: C, 50.71; H, 4.02; N, 3.29. Found: C, 50.69; H, 3.99; N, 3.16.

EXAMPLE 5

10-(3-cyanophenyl)-3,4,6,7,8,10-hexahydro-2H-thiopyrano[3,2-b]quinolin-9(5H)-one, 1,1-dioxide 3-Cyanobenzaldehyde (131 mg, 1.00 mmol) was processed as in Example 1 to provide the title compound. MS (APCI) m/e 355 (M+H)$^+$; $^1$H NMR (DMSO-d$_6$) 1.75 (m, 1H), 1.88 (m, 1H), 2.20 (m, 4H), 2.55 (m, 4H), 3.20 (m, 2H), 5.07 (s, 1H), 7.45 (t, 1H), 7.52 (s, 1H), 7.54 (dt, 1H), 7.60 (dt, 1H), 9.40 (br s, 1H); Anal. Calcd for C$_{19}$H$_{18}$N$_2$O$_3$S: C, 64.39; H, 5.12; N, 7.90. Found: C, 64.18; H, 5.15; N, 7.83.

EXAMPLE 6

3,4,6,7,8,10-hexahydro-10-[3-(trifluoromethyl) phenyl]-2H-thiopyrano[3,2-b]quinolin-9(5H)-one, 1,1-dioxide 3-Trifluoromethylbenzaldehyde (134 L, 1.00 mmol) was processed as in Example 1 to provide the title compound. MS (APCI) m/e 398 (M+H)$^+$; $^1$H NMR (DMSO-d$_6$) 1.74 (m, 1H), 1.90 (m, 1H), 2.20 (m, 4H), 2.55 (m, 4H), 3.18 (m, 2H), 5.11 (s, 1H), 7.48 (br s, 4H), 9.40 (br s, 1H); Anal. Calcd for C$_{19}$H$_{18}$F$_3$NO$_3$S: C, 57.42; H, 4.57; N, 3.52. Found: C, 57.12; H, 4.67; N, 3.39.

EXAMPLE 7

10-(3,4-difluorophenyl)-3,4,6,7,8,10-hexahydro-2H-thiopyrano[3,2-b]quinolin-9(5H)-one, 1,1-dioxide 3,4-Difluorobenzaldehyde (110 L, 1.00 mmol) was processed as in Example 1 to provide the title compound. MS (APCI) m/e 366 (M+H)$^+$; $^1$H NMR (DMSO-d$_6$) 1.75 (m, 1H), 1.88 (m, 1H), 2.20 (m, 4H), 2.50 (m, 4H), 3.20 (m, 2H), 5.02 (s, 1H), 7.02 (m, 1H), 7.10 (m, 1H), 7.26 (dt, 1H), 9.37 (br s, 1H); Anal. Calcd for C$_{18}$H$_{17}$F$_2$NO$_3$S: C, 59.17 H, 4.69; N, 3.83. Found: C, 58.91; H, 4.70; N, 3.69.

EXAMPLE 8

10-(3-bromophenyl)-3,4,6,7,8,10-hexahydro-2H-thiopyrano[3,2-b]quinolin-9(5H)-one, 1,1-dioxide 3-Bromobenzaldehyde (117 L, 1.00 mmol) was processed as in Example 1 to provide the title compound. MS (APCI) m/e 408 (M+H)$^+$, 410 (M+H)$^+$; $^1$H NMR (DMSO-d$_6$) 1.75 (m, 1H), 1.90 (m, 1H), 2.20 (m, 4H), 2.55 (m, 4H), 3.20 (m, 2H), 5.01 (s, 1H), 7.20 (m, 2H), 7.30 (m, 2H), 9.40 (br s, 1H); Anal. Calcd for C$_{18}$H$_{18}$BrNO$_3$S: C, 52.95; H, 4.44; N, 3.43. Found: C, 52.91; H, 4.53; N, 3.37.

EXAMPLE 9

3,4,6,7,8,10-hexahydro-10-(3,4,5-trifluorophenyl)-2H-thiopyrano[3,2-b]quinolin-9(5H)-one, 1,1-dioxide 3,4,5-Trifluorobenzaldehyde (160 mg, 1.00 mmol) was processed as in Example 1 to provide the title compound. MS (APCI) m/e 384 (M+H)$^+$; $^1$H NMR (DMSO-d$_6$) 1.75 (m, 1H), 1.88 (m, 1H), 2.20 (m, 4H), 2.50 (m, 4H), 3.20 (m, 2H), 5.02 (s, 1H), 7.00 (m, 2H), 9.41 (br s, 1H); Anal. Calcd for C$_{18}$H$_{16}$F$_3$NO$_3$S: C, 56.39; H, 4.21; N, 3.65. Found: C, 56.26; H, 4.27; N, 3.55.

EXAMPLE 10

10-[3-fluoro-5-(trifluoromethyl)phenyl]-3,4,6,7,8,10-hexahydro-2H-thiopyrano[3,2-b]quinolin-9(5H)-one, 1,1-dioxide 3-Fluoro-5-trifluoromethylbenzaldehyde (192 mg, 1.00 mmol) was processed as in Example 1 to provide the title compound. MS (APCI) m/e 416 (M+H)$^+$; $^1$H NMR (DMSO-d$_6$) 1.75 (m, 1H), 1.90 (m, 1H), 2.20 (m, 4H), 2.55 (m, 4H), 3.20 (m, 2H), 514 (s, 1H), 7.23 (d, 1H), 7.36 (s, 1H), 7.44 (d, 1H), 9.45 (br s, 1H); Anal. Calcd for C$_{19}$H$_{17}$F$_4$NO$_3$S: C, 54.94; H, 4.12; N, 3.37. Found: C, 54.84; H, 4.20; N, 3.26.

EXAMPLE 11

10-(3-fluorophenyl)-3,4,6,7,8,10-hexahydro-2H-thiopyrano[3,2-b]quinolin-9(5H)-one, 1,1-dioxide 3-Fluorobenzaldehyde (106 L, 1.00 mmol) was processed as in Example 1 to provide the title compound. MS (APCI) m/e 348 (M+H)$^+$; $^1$H NMR (DMSO-d$_6$) 1.75 (m, 1H), 1.88 (m, 1H), 2.20 (m, 4H), 2.55 (m, 4H), 3.20 (m, 2H), 5.05 (s, 1H), 6.93 (m, 2H), 7.04 (d, 1H), 7.25 (dt, 1H), 9.35 (br s, 1H); Anal. Calcd for C$_{18}$H$_{18}$FNO$_3$S: C, 62.23; H, 5.22; N, 4.03. Found: C, 61.95; H, 5.03; N, 3.89.

EXAMPLE 12

3,4,6,7,8,10-hexahydro-10-phenyl-2H-thiopyrano[3,2-b]quinolin-9(5H)-one, 1,1-dioxide Benzaldehyde (102 L, 1.00 mmol) was processed as in Example 1 to provide the title compound. MS (APCI) m/e 330 (M+H)$^+$; $^1$H NMR (DMSO-d$_6$) 1.73 (m, 1H), 1.90 (m, 1H), 2.20 (m, 4H), 2.50 (m, 4H), 3.18 (m, 2H), 5.03 (s, 1H), 7.10 (m, 1H), 7.20 (m, 4H), 9.28 (br s, 1H); Anal. Calcd for C$_{18}$H$_{19}$NO$_3$S: C, 65.63; H, 5.81; N, 4.25. Found: C, 65.57; H, 5.99; N, 4.12.

EXAMPLE 13

10-[4-fluoro-3-(trifluoromethyl)phenyl]-3,4,6,7,8,10-hexahydro-2H-thiopyrano[3,2-b]quinolin-9(5H)-one, 1,1-dioxide 4-Fluoro-3-trifluoromethylbenzaldehyde (194 mg, 1.01 mmol) was processed as in Example 1 to provide the title compound. MS (APCI) m/e 416 (M+H)$^+$; $^1$H NMR (DMSO-d$_6$) 1.75 (m, 1H), 1.90 (m, 1H), 2.22 (m, 4H), 2.52 (m, 4H), 3.20 (m, 2H), 509 (s, 1H), 7.38 (dd, 1H), 7.50 (m, 2H), 9.42 (br s, 1H); Anal. Calcd for C$_{19}$H$_{17}$F$_4$NO$_3$S: C, 54.93; H, 4.12; N, 3.37. Found: C, 54.77; H, 4.16; N, 3.26.

EXAMPLE 14

3,4,6,7,8,10-hexahydro-10-(4-methyl-3-nitrophenyl)2H-thiopyrano[3,2-b]quinolin-9(5H)-one, 1,1-dioxide 4-Methyl-3-nitrobenzaldehyde (165 mg, 1.00 mmol) was processed as in Example 1 to provide the title compound. MS (APCI) m/e 389 (M+H)$^+$; $^1$H NMR (DMSO-d$_6$) 1.75 (m, 1H), 1.88 (m, 1H), 2.22 (m, 4H), 2.45 (s, 3H), 2.55 (m, 4H), 3.20 (m, 2H), 5.09 (s, 1H), 7.35 (d, 1H), 7.43 (dd, 1H), 7.72 (d, 1H), 9.42 (br s, 1H); Anal. Calcd for C$_{19}$H$_{20}$N$_2$O$_5$S.0.25H$_2$O: C, 58.07; H, 5.25; N, 7.12. Found: C, 58.21; H, 5.36; N, 6.95.

EXAMPLE 15

10-(4-chloro-3-fluorophenyl)-3,4,6,7,8,10-hexahydro-2H-thiopyrano[3,2-b]quinolin-9(5H)-one, 1,1-dioxide 4-Chloro-3-fluorobenzaldehyde (159 mg, 1.00 mmol) was processed as in Example 1 to provide the title compound. MS (APCI) m/e 382 (M+H)$^+$; 384 (M+H)$^+$; $^1$H NMR (DMSO-d$_6$) 1.75 (m, 1H), 1.90 (m, 1H), 2.20 (m, 4H), 2.55 (m, 4H), 3.20 (m, 2H), 5.03 (s, 1H), 7.07 (m, 2H), 7.42 (t, 1H), 9.37 (br s, 1H); Anal. Calcd for C$_{18}$H$_{17}$ClFNO$_3$S: C, 56.62; H, 4.49; N, 3.67. Found: C, 56.36; H, 4.53; N, 3.59.

EXAMPLE 16

10-(3-chlorophenyl)-3,4,6,7,8,10-hexahydro-2H-thiopyrano[3,2-b]quinolin-9(5H)-one, 1,1-dioxide 3-Chlorobenzaldehyde (113 L, 1.00 mmol) was processed as in Example 1 to provide the title compound. MS (APCI) m/e 364 (M+H)$^+$, 366 (M+H)$^+$; $^1$H NMR (DMSO-d$_6$) 1.75 (m, 1H), 1.90 (m, 1H), 2.20 (m, 4H), 2.50 (m, 4H), 3.18 (m, 2H), 5.02 (s, 1H), 7.15 (m, 3H), 7.25 (m, 1H), 9.35 (br s, 1H); Anal. Calcd for C$_{18}$H$_{18}$ClNO$_3$S: C, 59.42; H, 4.99; N, 3.85. Found: C, 59.16; H, 5.13; N, 3.71.

EXAMPLE 17

3,4,6,7,8,10-hexahydro-10-[4-(trifluoromethyl)phenyl]-2H-thiopyrano[3,2-b]quinolin-9(5H)-one, 1,1-dioxide 4-Trifluoromethylbenzaldehyde (137 L, 1.00 mmol) was processed as in Example 1 to provide the title compound. MS (APCI) m/e 398 (M+H)$^+$; $^1$H NMR (DMSO-d$_6$) 1.75 (m, 1H), 1.89 (m, 1H), 2.20 (m, 4H), 2.50 (m, 4H), 3.19 (m, 2H), 5.10 (s, 1H), 7.38 (d, 2H), 7.58 (d, 2H), 9.37 (br s, 1H); Anal. Calcd for C$_{19}$H$_{18}$F$_3$NO$_3$S: C, 57.42; H, 4.56; N, 3.52. Found: C, 57.28; H, 4.58; N, 3.32.

EXAMPLE 18

10-(4-bromophenyl)-3,4,6,7,8,10-hexahydro-2H-thiopyrano[3,2-b]quinolin-9(5H)-one, 1,1-dioxide 4-Bromobenzaldehyde (185 mg, 1.00 mmol) was processed as in Example 1 to provide the title compound. MS (APCI) m/e 408 (M+H)$^+$; 410 (M+H)$^+$; $^1$H NMR (DMSO-d$_6$) 1.75 (m, 1H), 1.90 (m, 1H), 2.20 (m, 4H), 2.50 (m, 4H), 3.20 (m, 2H), 5.00 (s, 1H), 7.12 (d, 2H), 7.40 (d, 2H), 9.32 (br s, 1H); Anal. Calcd for C$_{18}$H$_{18}$BrNO$_3$S: C, 52.95; H, 4.44; N, 3.43. Found: C, 52.76; H, 4.34; N, 3.40.

EXAMPLE 19

10-(4-chloro-3-nitrophenyl)-3,4,6,7,8,10-hexahydro-2H-thiopyrano[3,2-b]quinolin-9(5H)-one, 1,1-dioxide 4-Chloro-3-nitrobenzaldehyde (185 mg, 1.00 mmol) was processed as in Example 1 to provide the title compound. MS (APCI) m/e 409 (M+H)$^+$, 411 (M+H)$^+$; $^1$H NMR (DMSO-d$_6$) 1.75 (m, 1H), 1.90 (m, 1H), 2.21 (m, 4H), 2.55 (m, 4H), 3.20 (m, 2H), 5.10 (s, 1H), 7.50 (dd, 1H), 7.63 (d, 1H), 7.75 (d, 1H), 9.45 (br s, 1H); Anal. Calcd for C$_{18}$H$_{17}$ClN$_2$O$_5$S: C, 52.88; H, 4.19; N, 6.85. Found: C, 52.59; H, 4.11; N, 6.72.

EXAMPLE 20

4-(3,4-dichlorophenyl)-4,6,7,8-tetrahydro-2-methyl-3-(methylsulfonyl)-5(1H)-quinolinone A solution of methanesulfonylacetone (135 mg, 1.00 mmol), 3,4-dichlorobenzaldehyde (175 mg, 1.00 mmol) and 3-amino-2-cyclohexen-1-one (111 mg, 1.00 mmol) in ethanol (7 mL) was heated to reflux for 24 hours and cooled. The solid that precipitated was collected, washed with ethanol, dried, and triturated with methanol to provide the title compound. MS (APCI) m/e 386 (M+H)$^+$, 388 (M+H)$^+$; $^1$H NMR (DMSO-d$_6$) 1.75 (m, 1H), 1.90 (m, 1H), 2.21 (m, 2H), 2.32 (s, 3H), 2.50 (m, 2H), 2.73 (s, 3H), 4.94 (s, 1H), 7.18 (dd, 1H), 7.34 (d, 1H), 7.53 (d, 1H), 9.48 (br s, 1H), Anal. Calcd for C$_{17}$H$_{17}$Cl$_2$NO$_3$S: C, 52.86; H, 4.44; N, 3.63. Found: C, 52.91; H, 4.31; N, 3.55.

EXAMPLE 21

4-(3-cyanophenyl)-4,6,7,8-tetrahydro-2-methyl-3-(methylsulfonyl)-5(1H)-quinolinone 3-Cyanobenzaldehyde (131 mg, 1.00 mmol) was processed as in Example 20 to provide the title compound. MS (APCI) m/e 343 (M+H)$^+$; $^1$H NMR (DMSO-d$_6$) 1.75 (m, 1H), 1.90 (m, 1H), 2.22 (m, 2H), 2.32 (s, 3H), 2.50 (m, 2H), 2.68 (s, 3H), 4.99 (s, 1H), 7.50 (m, 3H), 7.63 (dt, 1H), 9.48 (br s, 1H); Anal. Calcd for C$_{18}$H$_{18}$N$_2$O$_3$S: C, 63.14; H, 5.30; N, 8.18. Found: C, 63.15; H, 5.35; N, 8.11.

EXAMPLE 22

4-(3,4,5-trifluorophenyl)-4,6,7,8-tetrahydro-2-methyl-3-(methylsulfonyl)-5(1H)-quinolinone 3,4,5-Trifluoromethylbenzaldehyde (160 mg, 1.00 mmol) was processed as in Example 20 to provide the title compound. MS (APCI) m/e 370 (M−H)$^-$, 406 (M+Cl)$^-$; $^1$H NMR (DMSO-d$_6$) 1.75 (m, 1H), 1.90 (m, 1H), 2.22 (m, 2H), 2.33 (s, 3H), 2.52 (m, 2H), 2.76 (s, 3H), 4.97 (s, 1H), 7.00 (m, 2H), 9.51 (br s, 1H); Anal. Calcd for C$_{17}$H$_{16}$F$_3$NO$_3$S: C, 54.98; H, 4.34; N, 3.77. Found: C, 55.14; H, 4.16; N, 3.76.

EXAMPLE 23

4,6,7,8-tetrahydro-2-methyl-4-(4-methyl-3-nitrophenyl)-3-(methylsulfonyl)-5(1H)-quinolinone 4-Methyl-3-nitrobenzaldehyde (165 mg, 1.00 mmol) was processed as in Example 20 to provide the title compound. MS (APCI) m/e 377 (M+H)$^+$; $^1$H NMR (DMSO-d$_6$) 1.73 (m, 1H), 1.90 (m, 1H), 2.20 (m, 2H), 2.32 (s, 3H), 2.45 (s, 3H), 2.50 (m, 2H), 2.70 (s, 3H), 5.00 (s, 1H), 7.39 (d, 1H), 7.43 (dd, 1H), 7.75 (d, 1H), 9.48 (br s, 1H); Anal. Calcd for C$_{18}$H$_{20}$N$_2$O$_5$S: C, 57.43; H, 5.36; N, 7.44. Found: C, 57.41; H, 5.28; N, 7.48.

EXAMPLE 24

4-(4-chloro-3-nitrophenyl)-4,6,7,8-tetrahydro-2-methyl-3-(methylsulfonyl)-5(1H)-quinolinone 4-Chloro-3-nitrobenzaldehyde (185 mg, 1.00 mmol) was processed as in Example 20 to provide the title compound. MS (APCI) m/e 397 (M+H)$^+$; $^1$H NMR (DMSO-d$_6$) 1.75 (m, 1H), 1.90 (m, 1H), 2.22 (m, 2H), 2.33 (s, 3H), 2.50 (m, 2H), 2.78 (s, 3H), 5.02 (s, 1H), 7.50 (dd, 1H), 7.67 (d, 1H), 7.76 (d, 1H), 9.51 (br s, 1H); Anal. Calcd for C$_{17}$H$_{17}$ClN$_2$O$_5$S: C, 51.45; H, 4.32; N, 7.06. Found: C, 51.50; H, 4.26; N, 7.10.

EXAMPLE 25

4-(3-bromo-4-fluorophenyl)-4,6,7,8-tetrahydro-2-methyl-3-(methylsulfonyl)-5(1H)-quinolinone 3-Bromo-4-fluorobenzaldehyde (203 mg, 1.00 mmol) was processed as in Example 20 to provide the title compound. MS (APCI) m/e 414 (M+H)$^+$; $^1$H NMR (DMSO-d$_6$) 1.75 (m, 1H), 1.90 (m, 1H), 2.22 (m, 2H), 2.31 (s, 3H), 2.50 (m, 2H), 2.70 (s, 1H), 7.25 (m, 2H), 7.40 (dd, 1H), 9.47 (br s, 1H); Anal. Calcd for C$_{17}$H$_{17}$BrFNO$_3$S: C, 49.29; H, 4.14; N, 3.38. Found: C, 49.57; H, 3.93; N, 3.39.

EXAMPLE 26

4,6,7,8-tetrahydro-2-methyl-3-(methylsulfonyl)-4-(3-nitrophenyl)-5(1H)-quinolinone 3-Nitrobenzaldehyde (151 mg, 1.00 mmol) was processed as in Example 20 to provide the title compound. MS (APCI)

m/e 363 (M+H)$^+$; $^1$H NMR (DMSO-d$_6$) 1.70 (m, 1H), 1.90 (m, 1H), 2.32 (s, 3H), 2.50 (m, 2H), 2.70 (s, 3H), 5.07 (s, 1H), 7.57 (t, 1H), 7.65 (dt, 1H), 8.00 (m, 2H), 9.50 (br s, 1H); Anal. Calcd for C$_{17}$H$_{18}$N$_2$O$_5$S: C, 56.34; H, 5.01; N, 7.73. Found: C, 56.39; H, 4.92; N, 7.75.

EXAMPLE 27

4-(4-chloro-3-fluorophenyl)-4,6,7,8-tetrahydro-2-methyl-3-(methylsulfonyl)-5(1H)-quinolinone 4-Chloro-3-fluorobenzaldehyde (159 mg, 1.00 mmol) was processed as in Example 20 to provide the title compound. MS (APCI) m/e 370 (M+H)$^+$; $^1$H NMR (DMSO-d$_6$) 1.73 (m, 1H), 1.90 (m, 1H), 2.21 (m, 2H), 2.31 (s, 3H), 2.50 (m, 2H), 2.70 (s, 3H), 4.96 (s, 1H), 7.10 (m, 2H), 7.46 (t, 1H), 9.46 (br s, 1H); Anal. Calcd for C$_{17}$H$_{17}$ClFNO$_3$S: C, 55.21; H, 4.63; N, 3.79. Found: C, 55.07; H, 4.50; N, 3.67.

EXAMPLE 28

4,6,7,8-tetrahydro-2-methyl-3-(methylsulfonyl)-4-[4-(trifluoromethyl)phenyl]-5(1H)-quinolinone 4-Trifluoromethylbenzaldehyde (137 L, 1.00 mmol) was processed as in Example 20 to provide the title compound. MS (APCI) m/e 386 (M+H)$^+$; $^1$H NMR (DMSO-d$_6$) 1.72 (m, 1H), 1.90 (m, 1H), 2.21 (m, 1H), 2.31 (s, 3H), 2.50 (m, 3H), 2.63 (s, 3H), 5.02 (s, 1H), 7.41 (d, 2H), 7.61 (d, 2H), 9.65 (br s, 1H); Anal. Calcd for C$_{18}$H$_{18}$F$_3$NO$_3$S: C, 56.10; H, 4.71; N, 3.63. Found: C, 56.13; H, 4.61; N, 3.56.

EXAMPLE 29

9-(3,4-dichlorophenyl)-3,4,5,6,7,9-hexahydrothieno[3,2-b]quinolin-8(2H)-one, 1,1-dioxide A solution of tetrahydrothiophene-3-oxo-1,1-dioxide (144 mg, 1.07 mmol) prepared according to the method in *J. Heterocycl. Chem.*, v. 27 pp. 1453 (1990), 3,4-dichlorobenzaldehyde (175 mg, 1.00 mmol) and 3-amino-2-cyclohexen-1-one (111 mg, 1.00 mmol) in ethanol (7 mL) was heated to reflux for 24 hours. The precipitate was isolated, heated to reflux in toluene (5 mL) for 24 hours, and cooled. The solid that precipitated was collected, washed with toluene and ethanol and triturated to provide the title compound. MS (APCI) m/e 384 (M+H)$^+$; $^1$H NMR (DMSO-d$_6$) 1.75–2.0 (m, 2H), 2.23 (m, 2H), 2.57 (m, 2H), 2.85 (dt, 1H), 3.03 (dt, 1H), 3.38 (m, 2H), 4.84 (s, 1H), 7.17 (dd, 1H), 7.35 (d, 1H), 7.50 (d, 1H), 9.85 (br s, 1H); Anal. Calcd for C$_{17}$H$_{15}$Cl$_2$NO$_3$S: C, 53.14; H, 3.93; N, 3.64. Found: C, 52.97; H, 3.90; N, 3.56.

EXAMPLE 30

9-(3-cyanophenyl)-3,4,5,6,7,9-hexahydrothieno[3,2-b]quinolin-8(2H)-one, 1,1-dioxide 3-Cyanobenzaldehyde (136 mg, 1.04 mmol) was processed as in Example 29 to provide the title compound. MS (APCI) m/e 341 (M+H)$^+$; $^1$H NMR (DMSO-d$_6$) 1.88 (m, 2H), 2.22 (m, 2H), 2.56 (m, 2H), 2.85 (dtd, 1H), 3.03 (dt, 1H), 3.36 (m, 2H), 4.90 (s, 1H), 7.45 (td, 1H), 7.54 (dd, 1H), 7.56 (d, 1H), 7.61 (dd, 1H), 9.81 (br s, 1H); Anal. Calcd for C$_{18}$H$_{16}$N$_2$O$_3$S: C, 63.51; H, 4.73; N, 8.22. Found: C, 63.31; H, 4.61; N, 8.19.

EXAMPLE 31

9-[4-fluoro-3-(trifluoromethyl)phenyl]-3,4,5,6,7,9-hexahydrothieno[3,2-b]quinolin-8(2H)-one, 1,1-dioxide 4-Fluoro-3-trifluoromethylbenzaldehyde (130 L) was processed as in Example 29 to provide the title compound. MS (APCI) m/e 402 (M+H)$^+$; $^1$H NMR (DMSO-d$_6$) 1.88 (m, 2H), 2.23 (m, 2H), 2.55 (m, 2H), 2.85 (dtd, 1H), 3.03 (dt, 1H), 3.35 (m, 2H), 4.95 (s, 1H), 7.40 (dd, 1H), 7.52 (m, 2H), 9.60 (br s, 1H); Anal. Calcd for C$_{18}$H$_{15}$F$_4$NO$_3$S.0.25H$_2$O: C, 53.27; H, 3.85; N, 3.49. Found: C, 53.29; H, 3.74; N, 3.55

EXAMPLE 32

3,4,5,6,7,9-hexahydro-9-(4-methyl-3-nitrophenyl)thieno[3,2-b]quinolin-8(2H)-one, 1,1-dioxide 4-Methyl-3-nitrobenzaldehyde (165 mg, 1.00 mmol) was processed as in Example 29 to provide the title compound. MS (APCI) m/e 375 (M+H)$^+$; $^1$H NMR (DMSO-d$_6$) 1.88 (m, 2H), 2.23 (m, 2H), 2.45 (s, 3H), 2.56 (m, 2H), 2.85 (dtd, 1H), 3.03 (dt, 1H), 3.35 (m, 2H), 4.93 (s, 1H), 7.36 (d, 1H), 7.45 (dd, 1H), 7.72 (d, 1H), 9.83 (br s, 1H); Anal. Calcd for C$_{18}$H$_{18}$N$_2$O$_5$S.0.25H$_2$O: C, 57.06; H, 4.92; N, 7.39. Found: C, 57.24; H, 4.77; N, 7.23.

EXAMPLE 33

9-(3,4-difluorophenyl)-3,4,5,6,7,9-hexahydrothieno[3,2-b]quinolin-8(2H)-one, 1,1-dioxide 3,4-Difluorobenzaldehyde (110 L, 1.00 mmol) was processed as in Example 29 to provide the title compound. MS (APCI) m/e 352 (M+H)$^+$; $^1$H NMR (DMSO-d$_6$) 1.90 (m, 2H), 2.23 (m, 2H), 2.55 (m, 2H), 2.82 (dt, 1H), 3.02 (dt, 1H), 3.35 (m, 2H), 4.86 (s, 1H), 7.02 (m, 1H), 7.15 (ddd, 1H), 7.29 (dt, 1H), 9.79 (br s, 1H); Anal. Calcd for C$_{17}$H$_{15}$F$_2$NO$_3$S: C, 58.11; H, 4.30; N, 3.99. Found: C, 57.90; H, 3.96; N, 3.88.

EXAMPLE 34

9-(4-chloro-3-nitrophenyl)-3,4,5,6,7,9-hexahydrothieno[3,2-b]quinolin-8(2H)-one, 1,1-dioxide 4-Chloro-3-nitrobenzaldehyde (185 mg, 1.00 mmol) was processed as in Example 29 to provide the title compound. MS (APCI) m/e 393 (M–H)$^{31}$, 395 (M–H)$^-$; $^1$H NMR (DMSO-d$_6$) 1.90 (m, 2H), 2.23 (m, 2H), 2.55 (m, 2H), 2.85 (dtd, 1H), 3.01 (dt, 1H), 3.35 (m, 2H), 4.95 (s, 1H), 7.51 (dd, 1H), 7.64 (d, 1H), 7.79 (d, 1H), 9.88 (br s, 1H); Anal. Calcd for: C, 51.71; H, 3.38; N, 7.09. Found: C, 51.46; H, 3.86; N, 6.95.

EXAMPLE 35

1-[8-(3,4-dichlorophenyl)-3,4,5 8-tetrahydro-6-methyl-1,1-dioxido-2H-thiopyrano[3,2-b]pyridin-7-yl]ethanone A solution of tetrahydrothiopyran-3-one-1,1-dioxide (255 mg, 1.72 mmol), 3,4-dichlorobenzaldehyde (250 mg, 1.43 mmol) and 4-amino-3-penten-2-one (140 mg, 1.41 mmol) in ethanol (5 mL) was heated to reflux for 24 hours and cooled. The solid that precipitated was collected, washed with ethanol, and dried to provide the title compound. MS (APCI) m/e 386 (M+H)$^+$, 388 (M+H)$^+$; $^1$H NMR (DMSO-d$_6$) 2.19 (m, 2H), 2.20 (s, 3H), 2.30 (s, 3H), 2.50 (m, 2H), 3.20 (m, 2H), 5.07 (s, 1H), 7.15 (dd, 1H), 7.34 (d, 1H), 7.51 (d, 1H), 9.15 (br s, 1H); Anal. Calcd for C$_{17}$H$_{17}$Cl$_2$NO$_3$S: C, 52.86; H, 4.44; N, 3.63. Found: C, 52.74; H, 4.39; N, 3.64.

EXAMPLE 36

1-[8-(4-chloro-3-nitrophenyl)-3,4,5,8-tetrahydro-6-methyl-1,1-dioxido-2H-thiopyrano[3,2-b]pyridin-7-yl]ethanone 4-Chloro-3-nitrobenzaldehyde (220 mg, 1.19 mmol) was processed as in Example 35 to provide the title compound.

MS (APCI) m/e 397 (M+H)$^+$; $^1$H NMR (DMSO-d$_6$) 2.19 (m, 2H), 2.23 (s, 3H), 2.31 (s, 3H), 2.4–2.6 (m, 2H), 3.1–3.3 (m, 2H), 515 (s, 1H), 7.49 (dd, 1H), 7.64 (d, 1H), 7.76 (d, 1H), 9.19 (br s, 1H); Anal. Calcd for C$_{17}$H$_{17}$ClN$_2$O$_5$S: C, 51.45; H, 4.32; N, 7.06. Found: C, 51.18; H, 4.12; N, 7.03.

EXAMPLE 37

9-(3,4-dichlorophenyl)-3,4,5,6,7,9-hexahydrocyclopenta[b]thiopyrano[2,3-e]pyridin-8(2H)-one, 1,1-dioxide A solution of tetrahydrothiopyran-3-one-1,1-dioxide (175 mg, 1.20 mmol), 3,4-dichlorobenzaldehyde (175 mg, 1.00 mmol) and 3-amino-2-cyclopenten-1-one, prepared by the method described in *Synthesis*, p. 176 (1990)(101 mg, 1.05 mmol) in ethanol (5 mL) was heated to reflux for 24 hours, and cooled. The solid that precipitated was collected, washed with ethanol and dried to provide the title compound. MS (APCI) m/e 384 (M+H)$^+$; $^1$H NMR (DMSO-d$_6$) 2.25 (m, 4H), 2.60 (m, 4H), 3.20 (m, 2H), 4.82 (s, 1H), 7.20 (dd, 1H), 7.36 (d, 1H), 7.52 (d, 1H), 9.98 (br s, 1H); Anal. Calcd for C$_{17}$H$_{15}$Cl$_2$NO$_3$S.0.25H$_2$O: C, 52.52; H, 4.02; N, 3.60. Found: C, 52.36; H, 3.69; N, 3.63.

EXAMPLE 38

9-(4-chloro-3-nitrophenyl)-3,4,5,6,7,9-hexahydrocyclopenta[b]thiopyrano[2,3-e]pyridin-8(2H)-one, 1,1-dioxide 4-Chloro-3-nitrobenzaldehyde (187 mg, 1.01 mmol) was processed as in Example 37 to provide the title compound. MS (APCI) m/e 395 (M+H)$^+$; $^1$H NMR (DMSO-d$_6$) 2.25 (m, 4H), 2.60 (m, 4H), 3.24 (m, 2H), 4.93 (s, 1H), 7.55 (dd, 1H), 7.67 (d, 1H), 7.80 (d, 1H), 10.03 (br s, 1H); Anal. Calcd for C$_{17}$H$_{15}$ClN$_2$O$_5$S.0.25H$_2$O: C, 51.13; H, 3.91; N, 7.01. Found: C, 50.96; H, 4.02; N, 6.79.

EXAMPLE 39

9-(3-chloro-4-fluorophenyl)-3,4,5,6,7,9-hexahydrocyclopenta[b]thiopyrano[2,3-e]pyridin-8(2H)-one, 1,1-dioxide 3-Chloro-4-fluorobenzaldehyde (158 mg, 1.00 mmol) was processed as in Example 37 and recrystallized from methanol/ethyl acetate to provide the title compound. MS (APCI) m/e 368 (M+H)$^+$, 370 (M+H)$^+$; $^1$H NMR (DMSO-d$_6$) 2.25 (m, 4H), 2.62 (m, 4H), 3.20 (m, 2H), 4.93 (s, 1H), 7.20 (ddd, 1H), 7.30 (m, 2H), 9.96 (br s, 1H); Anal. Calcd for C$_{17}$H$_{15}$ClFNO$_3$S: C, 55.51; H, 4.11; N, 3.81. Found: C, 55.24; H, 3.85; N, 3.67.

EXAMPLE 40

9-(3-bromo-4-fluorophenyl)-3,4,5,6,7,9-hexahydrocyclopenta[b]thiopyrano[2,3-e]pyridin-8(2H)-one, 1,1-dioxide 3-Bromo-4-fluorobenzaldehyde (212 mg, 1.04 mmol) was processed as in Example 37 to provide the title compound. MS (APCI) m/e 412 (M+H)$^+$, 414 (M+H)$^+$; $^1$H NMR (DMSO-d$_6$) 2.25 (m, 4H), 2.60 (m, 4H), 3.20 (m, 2H), 4.83 (s, 1H), 7.25 (m, 2H), 7.41 (dd, 1H), 9.96 (br s, 1H); Anal. Calcd for C$_{17}$H$_{15}$BrFNO$_3$S.0.25H$_2$O: C, 48.99; H, 3.75; N, 3.36. Found: C, 48.98; H, 3.63; N, 3.28.

EXAMPLE 41

9-(3-nitrophenyl)-3,4,5 6,7,9-hexahydrothieno[3,2-b]quinolin-8(2H)-one, 1,1-dioxide 3-Nitrobenzaldehyde (153 mg, 1.01 mmol) was processed as in Example 29 to provide the title compound. MS (APCI) m/e 359 (M–H)$^-$; $^1$H NMR (DMSO-d$_6$) 1.83 (m, 1H), 1.92 (m, 1H), 2.24 (m, 2H), 2.57 (m, 2H), 2.85 (dtd, 1H), 3.05 (dt, 1H), 3.35 (m, 2H), 4.99 (s, 1H), 7.55 (t, 1H), 7.67 (dt, 1H), 7.98 (t, 1H), 8.03 (ddd, 1H), 9.91 (s, 1H); Anal. Calcd for C$_{17}$H$_{16}$N$_2$O$_5$S: C, 56.65; H, 4.47; N, 7.77. Found: C, 56.67; H, 4.35; N, 7.59.

EXAMPLE 42

9-(3-cyano)-3,4,5,6,7,9-hexahydrocyclopenta[b]thiopyrano[2,3-e]pyridin-8(2H)-one, 1,1-dioxide 3-Cyanobenzaldehyde (131 mg, 1.0 mmol) was processed as in Example 37 to provide the title compound. MS (APCI); m/e 339 (M–H)$^-$; $^1$H NMR (DMSO-d$_6$) 2.25 (m, 4H), 2.60 (m, 4H), 3.21 (m, 2H), 4.89 (s, 1H), 7.47 (t, 1H), 7.57 (dd, 1H), 7.57 (t, 1H), 7.59 (d, 1H), 7.64 (dt, 1H), 9.98 (br s, 1H); Anal. Calcd for C$_{18}$H$_{16}$N$_2$O$_3$S.0.25H$_2$O: C, 62.68; H, 4.82; N, 8.12. Found: C, 62.53; H, 4.53; N, 8.08.

EXAMPLE 43

9-(3-bromo-4-fluorophenyl)-3,4,5,6,7,9-hexahydrothieno[3,2-b]quinolin-8(2H)-one, 1,1-dioxide 3-Bromo-4-fluorobenzaldehyde (201 mg, 0.99 mmol) was processed as in Example 29 and recrystallized from methanol/chloroform to provide the title compound. MS (APCI); m/e 410 (M–H)$^-$, 412 (M–H)$^{31}$; $^1$H NMR (DMSO-d$_6$) 1.88 (m, 2H), 2.23 (m, 2H), 2.56 (m, 2H), 2.83 (dtd, 1H), 3.03 (dt, 1H), 3.33 (t, 2H), 4.85 (s, 1H), 7.22 (m, 2H), 7.40 (dd, 1H), 9.78 (br s, 1H); Anal. Calcd for C$_{17}$H$_{15}$BrFNO$_3$S: C, 49.52; H, 3.66; N, 3.39. Found: C, 49.19; H, 3.59; N, 3.24.

EXAMPLE 44

8-(4-chloro-3-nitrophenyl)-3,5,6,8-tetrahydro-2H-cyclopenta[b]thieno[2,3-e]pridin-7(4H)-one, 1,1-dioxide A solution of tetrahydrothiophene-3-oxo-1,1-dioxide (171 mg, 1.28 mmol), 4-chloro-3-nitrobenzaldehyde (210 mg, 1.13 mmol) and 3-amino-2-cyclopenten-1-one (110 mg, 1.13 mmol) in ethanol (3 mL) was heated to reflux for 24 hours and cooled. The precipitate was collected, washed with ethanol, dried and recrystallized from methanol/chloroform to provide the title compound. MS (APCI); m/e 379 (M–H)$^-$; $^1$H NMR (DMSO-d$_6$) 2.30 (t, 2H), 2.65 (m, 2H), 2.89 (dt, 1H), 3.05 (dt, 1H), 3.40 (t, 2H), 4.87 (s, 1H), 7.58 (dd, 1H), 7.68 (d, 1H), 7.88 (d, 1H), 10.4 (s, 1H); Anal. Calcd for C$_{16}$H$_{13}$ClN$_2$O$_5$S.0.25CH$_3$OH: C, 50.19; H, 3.62; N, 7.20. Found: C, 49.87; H, 3.26; N, 7.07.

EXAMPLE 45

10-(4-chloro-3-nitrophenyl)-3,4,6,7,10-hexahydro-2H,5H-bisthiopyrano[3,2-b:2',3'-e]pyridine, 1,1,9,9-tetraoxide A solution of tetrahydrothiopyran-3-one-1,1-dioxide (150 mg, 1.01 mmol), 4-chloro-3-nitrobenzaldehyde (95 mg, 0.51 mmol) and concentrated ammonium hydroxide (0.5 mL) was heated to 78° C. in ethanol (1 mL) for 24 hours in a sealed tube and cooled. The solid that precipitated was washed with ethanol, dried and triturated with hot acetone to provide the title compound. MS (APCI); m/e 443 (M–H)$^-$; $^1$H NMR (DMSO-d$_6$) 2.18 (m, 4H), 2.50 (m, 4H), 3.20 (m, 4H), 5.18 (s, 1H), 7.51 (dd, 1H), 7.69 (d, 1H), 7.76 (d, 1H), 9.24 (s, 1H); Anal. Calcd for C$_{17}$H$_{17}$ClN$_2$O$_6$S$_2$.0.15 NH$_4$OH: C, 45.36; H, 3.99 ; N, 6.72. Found: C, 45.71; H, 3.85; N, 7.02.

EXAMPLE 46

10-(3-pyridyl)-3,4,6,7,8,10-hexahydro-2H-thiopyrano[3,2-b]quinolin-9(5H)-one, 1,1-dioxide 3-Pyridinecarboxaldehyde (94 L, 1.0 mmol) was processed as in Example 1 with recrystallization from methanol to provide the title compound. MS (APCI); m/e 331 (M+H)$^+$; $^1$H NMR (DMSO-d$_6$) 1.75 (m, 1H), 1.90 (m, 1H), 2.20 (m, 4H), 2.53 (m, 4H), 3.20 (m, 2H), 5.03 (s, 1H), 7.25 (dd, 1H), 7.52 (dt, 1H), 8.31 (dd, 1H), 8.38 (d, 1H), 9.40 (br s, 1H); Anal. Calcd for $C_{17}H_{18}N_2O_3S.H_2O$: C, 58.60; H, 5.79; N, 8.04. Found: C, 58.79; H, 5.81; N, 7.63.

EXAMPLE 47

10-(4-pyridyl)-3,4,6,7,8,10-hexahydro-2H-thiopyrano[3,2-b]quinolin-9(5H)-one, 1,1-dioxide 4-Pyridinecarboxaldehyde (95 L, 1.0 mmol) was processed as in Example 1 and recrystallized from methanol to provide the title compound. MS (APCI); m/e 331 (M+H)$^+$; $^1$H NMR (DMSO-d$_6$) 1.75 (m, 1H), 1.90 (m, 1H), 2.20 (m, 4H), 2.53 (m, 4), 3.20 (m, 2H), 5.03 (s, 1H), 7.20 (d, 2H), 8.41 (d, 2H), 9.44 (br s, 1H); Anal. Calc $C_{17}H_{18}N_2O_3S$: C, 61.80; H, 5.49; N, 8.48. Found: C, 61.71; H, 5.40; N, 8.42.

EXAMPLE 48

9-(4-fluoro-3-trifluoromethyl)-3,4,5,6,7,9-hexahydrocyclopenta[b]thiopyrano[2,3-e]pyridin-8 (2H)-one, 1,1-dioxide 4-Fluoro-3-trifluoromethylbenzaldehyde (130 L) was processed as in Example 37 to provide the title compound. MS (APCI); m/e 400 (M–H)$^-$; $^1$H NMR (DMSO-d$_6$) 2.25 (m, 4H), 2.58 (m, 4H), 3.20 (m, 2H), 4.92 (s, 1H), 7.40 (dd, 1H), 7.54 (m, 2H), 9.96 (br s, 1H); Anal. Calcd for $C_{18}H_{15}F_4NO_3S$: C, 53.86; H, 3.77; N, 3.49. Found: C, 53.60; H, 3.82; N, 3.38.

EXAMPLE 49

9-(4-methyl-3-nitro)-3,4,5,6,7,9-hexahydrocyclopenta[b]thiopyrano[2,3-e]pyridin-8 (2H)-one, 1,1-dioxide 4-Methyl-3-nitrobenzaldehyde (165 mg, 1.00 mmol) was processed as in Example 37 to provide the title compound. MS (APCI); m/e 373 (M–H)$^-$; $^1$H NMR (DMSO-d$_6$) 2.24 (m, 4H), 2.45 (s, 3H), 2.60 (m, 4H), 3.20 (m, 2H), 4.90 (s, 1H), 7.38 (d, 1H), 7.46 (dd, 1H), 7.73 (d, 1H), 9.97 (br s, 1H); Anal. Calcd for $C_{18}H_{18}N_2O_5S$: C, 57.74; H, 4.85; N, 7.48. Found: C, 57.43; H, 4.72; N, 7.34.

EXAMPLE 50

9-(3,4-Difluorophenyl)-3,4,5,6,7,9-hexahydrocyclopenta[b]thiopyrano[2,3-e]pyridin-8 (2H)-one, 1,1-dioxide 3,4-Difluorobenzaldehyde (110 L) was treated according to the procedure described in Example 37 to provide 107 mg of the title compound as a white solid.

$^1$H NMR (DMSO-d$_6$) 2.25 (m, 4H), 2.60 (m, 4H), 3.20 (m, 2H), 4.83 (s, 1H), 7.05 (m, 1H), 7.16 (ddd, 1H), 7.30 (dt, 1H), 9.95 (br s, 1H);

MS(APCI–) m/z 350 (M–H)$^-$;

Anal. Calcd for $C_{17}H_{15}F_2NO_3S$: C, 58.11; H, 4.30; N, 3.98. Found: C, 58.10; H, 4.32; N, 3.94.

EXAMPLE 51

8-(4-Chloro-3-nitrophenyl)-2,3,4,5,6,8-hexahydrothieno[3,2-b:2i,3i-e]pyridine, 1,1,7,7-tetraoxide 4-Chloro-3-nitrobenzaldehyde (215 mg, 1.16 mmol), tetrahydrothiophene-3-oxo-1,1-dioxide (310 mg, 2.32 mmol) and 2.0 M $NH_3$ in ethyl alcohol (0.75 mL, 1.5 mmol) were heated in ethyl alcohol (4 mL) for 3 days at 80° C. in a sealed tube, cooled, the solid precipitate collected, and washed with ethyl alcohol. The solid was then heated to reflux in toluene with catalytic para-toluenesulfonic acid, cooled, the solid collected, washed with toluene, ethyl alcohol, methyl alcohol and dried. Trituration with hot methyl alcohol/chloroform (1:1) gave 184 mg of off-white solid.

$^1$H NMR (DMSO-d$_6$) 2.85 (m, 2H), 3.00 (dt, 2H), 3.40 (m, 4H), 5.12 (s, 1H), 7.63 (dd, 1H), 7.72 (d, 1H), 7.97 (d, 1H), 10.11 (br s, 1H);

MS (APCI–) m/z 415 (M–H)$^-$;

Anal. Calcd for $C_{15}H_{13}ClN_2O_6S_2$.0.1 toluene: C, 44.26; H, 3.26; N, 6.57. Found: C, 44.63; H, 3.06; N, 6.53.

EXAMPLE 52

8-(3-cyanophenyl)-2,3,4,5,6,8-hexahydro-7H-cyclopenta[b]thieno[2,3-e]pyridin-7-one, 1,1-dioxide 3-Cyanobenzaldehyde (206 mg, 1.57 mmol), tetrahydrothiophene-3-oxo-1,1-dioxide (212 mg, 1.58 mmol), and 3-amino-2-cyclopenten-1-one (150 mg, 1.55 mmol) were heated in ethanol (4 mL) to 80° C. for 3 days in a sealed tube, cooled, the solid precipitate collected and washed with ethanol. The solid was then heated to reflux in ethanol (10 mL) with 1N HCl in ether (0.5 mL) for 2 hours, cooled and the solvent evaporated. The crude oil was triturated with ethyl acetate, and the resultant solid collected, washed with ethyl acetate and dried to provide 252 mg of a tan solid. mp 156–176° C.;

$^1$H NMR (DMSO-d$_6$) 2.30 (t, 2H), 2.63 (m, 2H), 2.88 (dt, 1H), 3.07 (dt, 1H), 3.40 (t, 2H), 4.70 (s, 1H), 7.49 (t, 1H), 7.60 (d, 1H), 7.64 (s, 1H), 7.66 (dd, 1H), 10.38 (s, 1H);

MS (APCI–) m/z 325 (M–H)$^-$;

Anal. Calcd for $C_{17}H_{14}N_2O_3S$.0.33 EtOAc.0.75 $H_2O$: C, 59.64; H, 4.95; N, 7.59. Found: C, 59.32; H, 4.77; N, 7.41.

EXAMPLE 53

8-(3-Bromo-4-fluorophenyl)-2,3,4,5,6,8-hexahydrothieno[3,2-b:2i,3i-e]pyridine, 1,1,7,7-tetraoxide 3-Bromo-4-fluorobenzaldehyde (305 mg, 1.5 mmol), tetrahydrothiophene-3-oxo-1,1-dioxide (402 mg, 3.00 mmol), and 2.0 M $NH_3$ in ethanol (1.1 mL, 2.2 mmol) in ethanol (3 mL) were heated to 80° C. for 3 days in a sealed tube, cooled, the solid precipitate collected, and washed with ethanol. The solid was heated to reflux overnight in ethanol with 1.0 M HCl in ether (1 mL), cooled, the solid collected, washed with ethanol and dried to provide 185 mg of the title compound as an off-white solid.

$^1$H NMR (DMSO-d$_6$) 2.80 (m, 2H), 3.01 (dt, 2H), 3.35 (m, 4H), 4.97 (s, 1H), 7.30 (m, 2H), 7.53 (dd, 1H), 9.19 (br s, 1H);

MS (APCI–) m/z 432 (M–H)$^-$;

Anal. Calcd for $C_{15}H_{13}BrFNO_4S_2$: C, 41.48; H, 3.01; N, 3.22. Found: C, 41.61; H, 2.76; N, 3.14.

EXAMPLE 54

10-(3-Bromo-4-fluorophenyl)-3,4,6,7,8,10-hexahydro-2H,5H-dithiopyrano[3,2-b:2i.3i-e]pyridine, 1,1,9,9-tetraoxide 3-Bromo-4-fluorobenzaldehyde (202 mg, 1.0 mmol), tetrahydrothiopyran-3-one-1,1-dioxide (305 mg, 2.06 mmol) and 2.0 M $NH_3$ in ethanol (0.70 mL, 1.4 mmol) were heated in ethanol (3 mL) to 80° C. for 5 days in a sealed tube, cooled, the solid precipitate collected and washed with ethanol. The solid in toluene (10 mL) was then heated to reflux overnight, cooled, the solid collected, washed with ethanol and dried to provide 129 mg of the title compound as a white solid.

$^1$H NMR (DMSO-$d_6$) 2.17 (m, 4H), 2.50 (m, 4H), 3.18 (m, 4H), 5.09 (s, 1H), 7.24 (m, 2H), 7.38 (dd, 1H), 9.11 (s, 1H);

MS (APCI–) m/z 460 (M–H)⁻;

Anal. Calcd for $C_{17}H_{17}BrFNO_4S_2$: C, 44.16; H, 3.70; N, 3.02. Found: C, 43.97; H, 3.80; N, 2.95.

EXAMPLE 55

3,4,5,6,7,9-Hexahydro-9-(3-nitrophenyl)cyclopenta[b]thiopyrano[2,3-e]pyridin-8(2H)-one, 1,1-dioxide 3-Nitrobenzaldehyde (153 mg, 1.0 mmol), tetrahydrothiopyran-3-one-1,1-dioxide (148 mg, 1.00 mmol) and 3-amino-2-cyclopenten-1-one (97 mg, 1.00 mmol) were heated in ethanol (3 mL) to 80° C. for 5 days in a sealed tube, cooled, the solid precipitate collected, washed with ethanol and dried to provide 145 mg of the title compound as a tan solid.

mp>260° C.;

$^1$H NMR (DMSO-$d_6$) 2.25 (m, 4H), 2.60 (m, 4H), 3.23 (m, 2H), 4.98 (s, 1H), 7.57 (t, 1H), 7.69 (d, 1H), 8.00 (s, 1H), 8.04 (d, 1H), 10.03 (br s, 1H);

MS (APCI–) m/z 359 (M–H)⁻;

Anal. Calcd for $C_{17}H_{16}N_2O_5S$: C, 56.65; H, 4.47; N, 7.77. Found: C, 56.34; H, 4.44; N, 7.50.

EXAMPLE 56

8-(3-Bromo-4-fluorophenyl)-2,3,4,5,6,8-hexahydro-7H-cyclopenta[b]thieno[2,3-e]pyridin-7-one, 1,1-dioxide 3-Bromo-4-fluorobenzaldehyde (250 mg, 1.23 mmol) was treated according to the procedure described in Example 44, except that the heating phase was for 3 days and no recrystallization was necessary, to provide 241 mg of the title compound as an off-white solid.

mp>260° C.;

1H NMR (DMSO-$d_6$) 2.30 (t, 2H), 2.63 (m, 2H), 2.85 (dt, 1H), 3.06 (dt, 1H), 3.40 (t, 2H), 4.72 (s, 1H), 7.27 (m, 2H), 7.47 (d, 1H), 10.33 (br s, 1H);

MS (APCI–) m/z 396 (M–H)⁻;

Anal. Calcd for $C_{16}H_{13}BrFNO_3S$: C, 48.25; H, 3.29; N, 3.52. Found: C, 48.26; H, 3.17; N, 3.34.

EXAMPLE 57

8-(4-fluoro-3-trifluoromethylphenyl)-2,3,4,5,6,8-hexahydro-7H-cyclopenta[b]thieno[2,3-e]pyridin-7-one, 1,1-dioxide 4-Fluoro-3-trifluoromethylbenzaldehyde (0.20 mL), tetrahydrothiophene-3-oxo-1,1-dioxide (136 mg, 1.01 mmol) and 3-amino-2-cyclopenten-1-one (97 mg, 1.00 mmol) were heated in ethanol (4 mL) to 80° C. in a sealed tube for 3 days, cooled and the solvent evaporated. Flash chromatography over silica gel (10% methanol/chloroform) followed by trituration of the product with ethyl acetate provided the title compound as a white solid.

mp 254° C.;

1H NMR (DMSO-$d_6$) 2.30 (t, 2H), 2.65 (m, 2H), 2.88 (dt, 1H), 3.06 (dt, 1H), 3.40 (t, 2H), 4.85 (s, 1H), 7.41 (dd, 1H), 7.58 (m, 2H), 10.38 (s, 1H);

MS (APCI–) m/z 386 (M–H)⁻;

Anal. Calcd for $C_{17}H_{13}F_4NO_3S.0.25H_2O$: C, 52.10; H, 3.47; N, 3.57. Found: C, 52.13; H, 3.31; N, 3.47.

EXAMPLE 58

2,3,4,5,6,8-Hexahydro-8-(3-nitrophenyl)-7H-cyclopenta[b]thieno[2,3-e]pyridin-7-one, 1,1-dioxide 3-Nitrobenzaldehyde (225 mg, 1.49 mmol), tetrahydrothiophene-3-oxo-1,1-dioxide (202 mg, 1.51 mmol) and 3-amino-2-cyclopenten-1-one (144 mg, 1.48 mmol) were heated in ethanol (5 mL) to 80° C. in a sealed tube for 3 days, cooled, and the solid precipitate filtered off. The filtrate was treated with 1.0 M HCl in ether (0.1 mL), heated to reflux for 1.5 hours, cooled and solvent evaporated. Recrystallization from ethanol provided 130 mg of the title compound as a light yellow solid.

$^1$H NMR (DMSO-$d_6$) 2.31 (t, 2H), 2.65 (m, 2H), 2.90 (dt, 1H), 3.08 (dt, 1H), 3.40 (t, 2H), 4.90 (s, 1H), 7.58 (t, 1H), 7.73 (dt, 1H), 8.05 (m, 2H), 10.41 (s, 1H);

MS (APCI–) m/z 345 (M–H)⁻;

Anal. Calcd for $C_{16}H_{14}N_2O_5S$: C, 55.48; H, 4.07; N, 8.08. Found: C, 55.37; H, 4.02; N, 7.88.

EXAMPLE 59

3,4,6,7,8,10-Hexahydro-10-(3-nitrophenyl)-2H,5H-dithiopyrano[3,2-b:2i,3i-e]pyridine, 1,1,9,9-tetraoxide 3-Nitrobenzaldehyde (153 mg, 1.0 mmol) was treated according to the procedure described in Example 54 to provide 188 mg of the title compound as a white solid.

mp>260° C.;

$^1$H NMR (DMSO-$d_6$) 2.19 (m, 4H), 2.52 (m, 4H), 3.20 (m, 4H), 5.23 (s, 1H), 7.60 (t, 1H), 7.68 (d, 1H), 7.98 (s, 1H), 8.08 (d, 1H), 9.23 (br s, 1H);

MS (APCI–) m/z 409 (M–H)⁻;

Anal. Calcd for $C_{17}H_{18}N_2O_6S_2$: C, 49.75; H, 4.42; N, 6.82. Found: C, 49.58; H, 4.34; N, 6.79.

EXAMPLE 60

8-(3,4-Dichlorophenyl)-2,3,4,5,6,8-hexahydro-7H-cyclopenta[b]thieno[2,3-e]pyridin-7-one, 1,1-dioxide 3,4-Dichlorobenzaldehyde (175 mg, 1.0 mmol) was treated according to the procedure described in Example 52 to provide 204 mg of the title compound as a white solid.

mp>260° C.;

$^1$H NMR (DMSO-$d_6$) 2.30 (t, 2H), 2.63 (m, 2H), 2.87 (dt, 1H), 3.05 (dt, 1H), 3.40 (t, 2H), 4.72 (s, 1H), 7.22 (dd, 1H), 7.41 (d, 1H), 7.52 (d, 1H), 10.36 (br s, 1H);

MS (APCI–) m/z 368 (M–H)⁻;

Anal. Calcd for $C_{16}H_{13}Cl_2NO_3S$: C, 51.90; H, 3.54; N, 3.78. Found: C, 51.93; H, 3.59; N, 3.53.

EXAMPLE 61

8-(3-Chloro-4-fluorophenyl)-2,3,4,5,6,8-hexahydro-7H-cyclopenta[b]thieno[2,3-e]pyridin-7-one, 1,1-dioxide 3-Chloro-4-fluorobenzaldehyde (0.16 mL) was treated according to the procedure described in Example 56 to provide 107 mg of the title compound as a white solid.

$^1$H NMR (DMSO-$d_6$) 2.30 (t, 2H), 2.64 (m, 2H), 2.85 (dt, 1H), 3.05 (dt, 1H), 3.39 (t, 2H), 4.72 (s, 1H), 7.23 (m, 1H), 7.28 (m, 1H), 7.37 (d, 1H), 10.31 (br s, 1H);

MS (APCI–) m/z 352 (M–H)$^-$;

Anal. Calcd for $C_{16}H_{13}ClFNO_3S$: C, 54.32; H, 3.70; N, 3.96. Found: C, 54.34; H, 3.68; N, 3.85.

EXAMPLE 62

8-(3-Cyanophenyl)-2,3,4,5,6,8-hexahydrothieno[3,2-b:2i,3i-e]pyridine, 1,1,7,7-tetraoxide 3-Cyanobenzaldehyde (132 mg, 1.01 mmol), tetrahydrothiophene-3-oxo-1,1-dioxide (272 mg, 2.03 mmol) and 2.0 M $NH_3$ in ethanol (0.75 mL, 1.5 mmol) were heated to 80° C. in ethanol (4 mL) in a sealed tube for 3 days, cooled, treated with 1.0 M HCl in ether (1 mL), heated to reflux for 1 hour, cooled and solvent evaporated. The crude was flash chromatographed over silica gel (15% methanol/chloroform), and the product triturated with ethyl acetate to provide 87 mg of the title compound as an off-white solid.

mp 248° C.;

$^1$H NMR (DMSO-$d_6$) 2.83 (dt, 2H), 3.02 (dt, 2H), 3.40 (m, 4H), 5.03 (s, 1H), 7.50 (t, 1H), 7.61 (d, 1H), 7.70 (d, 1H), 7.73 (s, 1H), 10.07 (br s, 1H);

MS (APCI–) m/z 361 (M–H)$^-$;

Anal. Calcd for $C_{16}H_{14}N_2O_4S_2 \cdot 0.33EtOAc \cdot 0.6H_2O$: C, 51.71; H, 4.47; N, 6.96. Found: C, 51.84; H. 4.21; N, 6.61.

EXAMPLE 63

8-(2-Cyano-4-pyridinyl)-2,3,4,5,6,8-hexahydro-7H-cyclopenta[b]thieno[2,3-e]pyridin-7-one, 1,1-dioxide 2-Cyanopyridine-4-carboxaldehyde (0.20 g, 1.52 mmol), prepared according to the method of Ashimori (*Chem Pharm Bull* 1990, 38, 2446), tetrahydrothiophene-3-oxo-1,1-dioxide (241 mg, 1.8 mmol) and 3-amino-2-cyclopenten-1-one (0.146 g, 1.5 mmol) were heated to 40–50° C. in isopropanol for 3 days, cooled, solvent evaporated and flash chromatographed (10% methanol/methylene chloride). The product was dissolved in isopropanol, treated with 1.0 M HCl in ether (1.5 mL), heated to 50° C. for 10 minutes, cooled and solvent evaporated. The residue was triturated with ether, collected, washed with ether and dried to provided 63.5 mg of the title compound as a light-yellow powder.

$^1$H NMR (DMSO-$d_6$) 2.30 (t, 2H), 2.65 (m, 2H), 3.02 (m, 2H), 3.45 (t, 2H), 4.85 (s, 1H). 7.64 (d, 1H), 7.94 (s, 1H), 8.65 (d, 1H), 10.48 (s, 1H);

MS (APCI–) m/z 326 (M–H)$^-$;

Anal. Calcd for $C_{16}H_{13}N_3O_3S \cdot 0.42\ C_2H_6O \cdot 0.25\ H_2O \cdot 0.15\ HCl$: C, 57.31; H, 4.48; N, 11.62; Cl, 1.47. Found: C, 57.63; H, 4.74; N, 11.22; Cl, 1.37.

EXAMPLE 64

8-(3-Bromophenyl)-2,3,4,5,6,8-hexahydro-7H-cyclopenta[b]thieno[2,3-e]pyridin-7-one, 1,1-dioxide 3-Bromobenzaldehyde (0.12 mL, 1.0 mmol), tetrahydrothiophene-3-oxo-1,1-dioxide (137 mg, 1.02 mmol) and 3-amino-2-cyclopenten-1-one (98 mg, 1.0 mmol) were heated in ethanol (4 mL) to 80° C. in a sealed tube for 3 days, then treated with 1.0 M HCl in ether (0.5 mL), heated to reflux for 3 hours, cooled and solvent evaporated. The crude was flash chromatographed over silica gel (10% methanol/chloroform) and the product triturated with ethyl acetate to provide 147 mg of the title compound as an off-white solid.

mp 246° C.;

$^1$H NMR (DMSO-$d_6$) 2.32 (t, 2H), 2.65 (m, 2H), 2.85 (dt, 1H), 3.07 (dt, 1H), 3.40 (t, 2H), 4.69 (s, 1H), 7.22 (m, 2H), 7.36 (m, 2H), 10.33 (br s, 1H);

MS (APCI–) m/z 378 (M–H)$^-$;

Anal. Calcd for $C_{16}H_{14}BrNO_3S$: C, 50.54; H, 3.71; N, 3.68. Found: C, 50.62; H, 3.63; N, 3.54.

EXAMPLE 65

8-(4-Fluoro-3-trifluoromethylphenyl)-2,3,4,5,6,8-hexahydrothieno[3,2-b:2i,3i-e]pyridine, 1,1,7,7-tetraoxide 4-Fluoro-3-trifluoromethylbenzaldehyde (0.19 mL) was treated according to the procedure described in Example 62 to provide 35 mg of the title compound as a white solid.

mp>260° C.;

$^1$H NMR (DMSO-$d_6$) 2.83 (dtd, 2H), 3.02 (dt, 2H), 3.39 (m, 4H), 5.11 (s, 1H), 7.45 (dd, 1H), 7.62 (d, 1H), 7.67 (m, 1H), 10.07 (br s, 1H);

MS (APCI–) m/z 422 (M–H)$^-$;

Anal. Calcd for $C_{16}H_3F_4NO_4S_2$: C, 45.39; H, 3.09; N, 3.31. Found: C, 45.23; H, 2.87; N, 3.12.

EXAMPLE 66

1-[8-(3-Bromo-4-fluorophenyl)-3,4,5,8-tetrahydro-6-methyl-1,1-dioxido-2H-thiopyrano[3,2-b]pyridin-7-yl)]ethan-1-one 3-Bromo-4-fluorobenzaldehyde (246 mg, 1.21 mmol) was treated according to the procedure described in Example 35 to provide 325 mg of the title compound as a white solid.

mp>260° C.;

$^1$H NMR (DMSO-$d_6$) 2.17 (m, 2H), 2.20 (s, 3H), 2.30 (s, 3H), 2.50 (m, 2H), 3.20 (m, 2H), 5.06 (s, 1H), 7.20 (m, 2H), 7.40 (dd, 1H), 9.11 (s, 1H);

MS (APCI–) m/z 412 (M–H)$^-$;

Anal. Calcd for C17H17BrFNO3S: C, 49.28; H, 4.13; N, 3.38. Found: C, 49.06; H, 4.10; N, 3.28.

EXAMPLE 67

8-(4-Bromo-2-thienyl)-2,3,4,5,6,8-hexahydro-7H-cyclopenta[b]thieno[2,3-e]pyridin-7-one, 1,1-dioxide 4-Bromothiophene-2-carboxaldehyde (500 mg, 2.6 mmol), tetrahydrothiophene-3-oxo-1,1-dioxide (295 mg, 2.2 mmol) and 3-amino-2-cyclopenten-1-one (215 mg, 2.2 mmol) were heated in ethyl alcohol (5 mL) to 80° C. in a sealed tube for 2 days, cooled, the solid precipitate collected, washed with ethanol, dissolved in a solution of methanol/ methylene chloride 1:3, filtered through cotton, concentrated on a steam bath and allowed to crystallize to provide 0.34 g of the title compound as a light brown solid.

mp 254–255° C.;

$^1$H NMR (DMSO-d$_6$) 2.35 (t, 2H), 2.53–2.75 (m, 2H), 2.78–2.91 (m, 1H), 2.97–3.10 (m, 1H), 3.42 (t, 2H), 4.95 (s, 1H), 6.88 (d, 1H), 7.46 (d, 1H), 10.43 (bs, 1H);

MS (APCI+) m/z 386 (M+H)$^+$, 403 (M+NH4)$^+$, MS (APCI-) m/z 384 (M-H)$^-$;

Anal. Calcd for C$_{14}$H$_{12}$NO$_3$S$_2$Br: C, 43.53; H, 3.13; N, 3.63. Found: C, 43.39; H, 2.84; N, 3.41.

EXAMPLE 68

8-(5-Bromo-2-thienyl)-2,3,4,5,6,8-hexahydro-7H-cyclopenta[b]thieno[2,3-e]pyridin-7-one, 1,1-dioxide 5-Bromothiophene-2-carboxaldehyde (500 mg, 2.6 mmol), was treated according to the procedure described in Example 67 to provide 0.297 g of the title compound as a brown solid.

mp 246–247° C.;

$^1$H NMR (DMSO-d$_6$) 2.35 (t, 2H), 2.52–2.73 (m, 2H), 2.78–2.90 (m, 1H), 2.95–3.08 (m, 1H), 3.41 (t, 2H), 4.92 (s, 1H), 6.73 (d, 1H), 6.97 (d, 1H), 10.39 (s, 1H);

MS (APCI-) m/z 384 (M-H)$^-$;

Anal. Calcd for C$_{14}$H$_{12}$NO$_3$S$_2$Br: C, 43.53; H, 3.13; N, 3.63. Found: C, 43.19; H, 3.16; N, 3.31.

EXAMPLE 69

2,3,4,5,6,8-Hexahydro-8-(5-nitro-3-thienyl)-7H-cyclopenta[b]thieno[2,3-e]pyridin-7-one, 1,1-dioxide 2-Nitrothiophene-4-carboxaldehyde (0.41 g, 2.6 mmol) was treated according to the procedure described in Example 67 to provide 0.423 g of the title compound as a brown powder.

$^1$H NMR (DMSO-d$_6$) 2.34 (t, 2H), 2.52–2.74 (m, 2H), 2.80–2.92 (m, 1H), 2.98–3.11 (m, 1H), 3.43 (t, 2H), 4.84 (s, 1H), 7.78 (d, 1H), 7.94 (d, 1H), 10.39 (s, 1H);

MS (APCI+) m/z 353 (M+H)$^+$, 370 (M+NH$_4$)$^+$, MS (APCI-) m/z 351 (M-H)$^-$;

Anal. Calcd for C$_{14}$H$_{12}$N$_2$O$_5$S$_2$: C, 47.72; H, 3.43; N, 7.95. Found: C, 47.43; H, 3.22 N, 7.65.

EXAMPLE 70

2,3,4,5,6,8-Hexahydro-8-(5-nitro-2-thienyl)-7H-cyclopenta[b]thieno[2,3-e]pyridin-7-one, 1,1-dioxide 5-Nitrothiophene-2-carboxaldehyde (205 mg, 1.30 mmol) was treated according to the procedure described in Example 67 to provide 238 mg of the title compound as a brown solid.

mp 251–254° C.;

$^1$H NMR (DMSO-d$_6$) 2.37 (t, 2H), 2.56–2.78 (m, 2H), 2.83–2.96 (m, 1H), 3.01–3.14 (m, 1H), 3.46 (t, 2H), 5.07 (s, 1H), 7.10 (d, 1H), 7.97 (d, 1H), 10.59 (s, 1H);

MS (APCI+) m/z 353 (M+H)$^+$, 370 (M+NH$_4$)$^+$, (APCI-) m/z 351 (M-H)$^-$;

Anal. Calcd for C$_{14}$H$_{12}$N$_2$O$_5$S$_2$: C, 47.72; H, 3.43; N, 7.95. Found: C, 47.39; H, 3.39; N, 7.67.

EXAMPLE 71

2,3,4,5,6,8-Hexahydro-8-(5-nitro-2-furyl)-7H-cyclopenta[b]thieno[2,3-e]pyridin-7-one, 1,1-dioxide 5-Nitro-2-furaldehyde (185 mg, 1.30 mmol) was treated according to the procedure described in Example 67 to provide 117 mg of the title compound as a brown solid.

$^1$H NMR (DMSO-d$_6$) 2.38 (t, 2H), 2.57–2.79 (m, 2H), 2.83–2.96 (m, 1H), 2.96–3.09 (m, 1H), 3.43 (t, 2H), 4.96 (s, 1H), 6.71 (d, 1H), 7.65 (d, 1H), 10.52 (s, 1H);

MS (APCI+) m/z 337 (M+H)$^+$, 354 (M+NH$_4$)$^+$, MS (APCI-) m/z 335 (M-H)$^-$;

Anal. Calcd for C$_{14}$H$_{12}$N$_2$O$_6$S: C, 50.00; H, 3.60; N, 8.33. Found: C, 49.80; H, 3.42; N, 8.14.

EXAMPLE 72

8-(3 4-Dibromophenyl)-2,3,4,5,6,8-hexahydro-7H-cyclopenta[b]thieno[2,3-e]pyridin-7-one, 1,1-dioxide 3,4-Dibromobenzaldehyde (293 mg, 1.11 mmol), tetrahydrothiophene-3 -oxo-1,1-dioxide (146 mg, 1.09 mmol) and 3-amino-2-cyclopenten-1-one (107 mg, 1.10 mmol) were heated in ethanol (4 mL) to 80° C. in a sealed tube for 3 days, cooled, the solid precipitate collected, washed with ethanol and dried to provide 211 mg of the title compound. The filtrate was treated with 1.0 M HCl in ether (1 mL), heated to reflux for 2 hours, cooled and solvent evaporated. The residue was treated with ethanol, heated and the resultant solid collected, washed with ethanol and dried to provide an additional 29 mg of the title compound. The two lots of material were combined, triturated with hot ethyl acetate, collected, washed with ethyl acetate and dried to provide 197 mg of the title compound as a tan solid.

mp>260° C.;

$^1$H NMR (DMSO-d$_6$) 2.30 (t, 2H), 2.55–2.75 (m, 4H), 2.85 (dt, 1H), 3.05 (dt, 1H), 3.40 (t, 2H), 4.71 (s, 1H), 7.17 (dd, 1H), 7.54 (d, 1H), 7.65 (d, 1H), 10.36 (br s, 1H);

MS (APCI-) m/z 458 (M-H)$^-$;

Anal. Calcd for C$_{16}$H$_{13}$Br$_2$NO$_3$S: C, 41.85; H, 2.85; N, 3.05. Found: C, 41.79; H, 2.75; N, 2.78.

EXAMPLE 73

2,3,4,5,6,8-Hexahydro-8-(3-nitrophenyl)dithieno[3,2-b:2i,3i-e]pyridine 1,1,7,7-tetraoxide 3-Nitrobenzaldehyde (155 mg, 1.03 mmol), tetrahydrothiophene-3-oxo-1,1-dioxide (273 mg, 2.04 mmol) and 2.0 M NH$_3$ in ethanol (0.7 mL, 1.4 mmol) were heated to 80° C. in ethanol (4 mL) for 3 days in a sealed tube, cooled, treated with 1.0 M HCl in ether (1 mL), heated to reflux for 15 minutes, cooled, the solid precipitate collected, washed with ethanol and dried. The solid was triturated with hot ethyl acetate, collected, washed with ethyl acetate and dried to provide 174 mg of the title compound as an orange-yellow solid.

mp 248–252° C.;

$^1$H NMR (DMSO-d$_6$) 2.85 (m, 2H), 3.05 (m, 2H), 3.40 (m, 4H), 5.15 (s, 1H), 7.61 (t, 1H), 7.77 (dt, 1H), 8.10 (m, 2H), 10.09 (br s, 1H);

MS (APCI-) m/z 381 (M-H)$^-$;

Anal. Calcd for C$_{15}$H$_{14}$N$_2$O$_6$S$_2$: C, 47.11; H, 3.68; N, 7.32. Found: C, 47.47; H, 3.68; N, 7.29.

EXAMPLE 74

8-(3-Chloro-4-fluorophenyl)-2,3,4,5,6,8-hexahydrothieno[3,2-b:2i,3i-e]pyridine, 1,1,7,7-tetraoxide 3-Chloro-4-fluorobenzaldehyde (160 mg, 1.0 mmol), tetrahydrothiophene-3-oxo-1,1-dioxide (273 mg, 2.04 mmol) and 2.0 M $NH_3$ in ethanol (0.7 mL, 1.4 mmol) were heated to 80° C. in ethanol (4 mL) for 3 days in a sealed tube, cooled, the solid precipitate collected, washed with ethanol and dried to provide 146 mg of the title compound as a light-yellow solid.

mp>260° C.

$^1$H NMR (DMSO-$d_6$) 2.82 (dt, 2H), 3.02 (dt, 2H), 3.38 (m, 4H), 4.97 (s, 1H), 7.24–7.38 (m, 2H), 7.43 (dd, 1H), 9.35 (br s, 1H);

MS (APCI−) m/z 388 (M−H)$^−$;

Anal. Calcd for $C_{15}H_{13}ClFNO_4S_2$: C, 46.09; H, 3.61; N, 3.58. Found: C, 45.91; H, 3.40; N, 3.63.

EXAMPLE 75

4-(3,4-Dichlorophenyl)-1,4,6,7-tetrahydro-2-methyl-3-(methylsulfonyl)-5H-cyclopenta[b]pyridin-5-one 3,4-Dichlorobenzaldehyde (175 mg, 1.0 mmol), methanesulfonylacetone (137 mg, 1.01 mmol) and 3-aminocyclopentenone (95 mg, 0.98 mmol) were heated to 80° C. in ethanol (4 mL) in a sealed tube for 3 days, cooled and the solvent evaporated. The crude material was flash chromatographed on silica gel (5% methanol/chloroform) to provide 80 mg of the title compound as a tan solid.

mp 218–220° C.;

$^1$H NMR (CDCl$_3$) 2.48–2.50 (br s, 5H), 2.59 (s, 3H), 2.63 (m, 2H), 5.01 (s, 1H), 6.53 (br s, 1H), 7.25 (m, 1H), 7.48 (m, 2H);

MS (APCI−) m/z 370 (M−H)$^−$;

Anal. Calcd for $C_{16}H_5Cl_2NO_3S$: C, 51.62; H, 4.06; N, 3.76. Found: C, 51.36; H, 3.99; N, 3.83.

EXAMPLE 76

4-(4-Chloro-3-nitrophenyl)-1,4,6,7-tetrahydro-2-methyl-3-(methylsulfonyl)-5H-cyclopenta[b]pyridin-5-one 4-Chloro-3-nitrobenzaldehyde (186 mg, 1.0 mmol) was treated according to the procedure described in Example 75 to provide 105 mg of the title compound as an off-white solid.

mp 232° C.;

$^1$H NMR (DMSO-$d_6$) 2.27 (m, 2H), 2.36 (s, 3H), 2.58 (m, 2H), 2.83 (s, 3H), 4.87 (s, 1H), 7.53 (dd, 1H), 7.70 (d, 1H), 7.80 (d, 1H), 10.10 (s, 1H);

MS (APCI−) m/z 381 (M−H)$^−$;

Anal. Calcd for $C_{16}H_{15}ClN_2O_5S$: C, 51.62; H, 4.06; N, 3.76. Found: C, 51.36; H, 3.99; N, 3.83.

EXAMPLE 77

8-(3,4-Chlorophenyl)-2,3,4,5,6,8-hexahydrothieno[3,2-b:2i,3i-e]pyridine, 1,1,7,7-tetraoxide 3,4-Dichlorobenzaldehyde (196 mg)) was treated according to the procedure described in Example 74 to provide 165 mg of the title compound as a light-yellow solid.

mp>260° C.;

$^1$H NMR (DMSO-$d_6$) 2.82 (m, 2H), 3.00 (dt, 2H), 3.39 (m, 4H), 4.97 (s, 1H), 7.26 (dd, 1H), 7.49 (d, 1H), 7.55 (d, 1H), 9.53 (br s, 1H);

MS (APCI−) m/z 404 (M−H)$^−$;

Anal. Calcd for $C_{15}H_{13}Cl_2NO_4S_2$: C, 44.34; H, 3.22; N, 3.44. Found: C, 43.99; H, 3.11; N, 3.68.

EXAMPLE 78

8-(4-Bromophenyl)-2,3,4,5,6,8-hexahydro-7H-cyclolpenta[b]thieno[2,3-e]pyridin-7-one, 1,1-dioxide 4-Bromobenzaldehyde (377 mg, 2.00 mmol) tetrahydrothiophene-3-oxo-1,1-dioxide (230 mg, 1.7 mmol) and 3-amino-2-cyclopenten-1-one (165 mg, 1.7 mmol) were heated to 80° C. in a sealed tube for 2 days, cooled, the solid precipitate collected, and washed with ethanol. The filtrate was treated with 1.0 M HCl/diethyl ether (4 mL), heated to reflux for 15 minutes, cooled, concentrated, combined with the solid precipitate and purified by flash chromatography over silica gel (5% methanol/methylene chloride). The product was crystallized from ethanol to provide 218 mg of the title compound.

mp 253–256° C.;

$^1$H NMR (DMSO-$d_6$) 2.30 (t, 2H), 2.51–2.72 (m, 2H), 2.79–2.91 (m, 1H), 2.97–3.09 (m, 1H), 3.34–3.42 (m, 2H), 4.66 (s, 1H), 7.17 (d, 2H), 7.43 (d, 2H), 10.27 (s, 1H);

MS (APCI+) m/z 380 (M+H)$^+$, MS (APCI−) m/z 378 (M−H)$^−$;

Anal. Calcd for $C_{16}H_{14}BrNO_3S$: C, 50.54; H, 3.71; N, 3.68. Found: C, 50.50; H, 3.74; N, 3.52.

EXAMPLE 79

8-(3,4-Difluorophenyl)-2,3,4,5,6,8-hexahydro-7H-cyclopenta[b]thieno[2,3-e]pyridin-7-one, 1,1-dioxide 3,4-Difluorobenzaldehyde (162 mg) was treated according to the procedure described in Example 56 to provide 169 mg of the title compound as a white powder.

mp>260° C.

$^1$H NMR (DMSO-$d_6$) 2.30 (t, 2H), 2.5–2.75 (m, 2H), 2.86 (dt, 1H), 3.07 (dt, 1H), 3.40 (t, 2H), 4.72 (s, 1H), 7.08 (m, 1H), 7.18–7.36 (m, 2H), 10.32 (br s, 1H);

MS (APCI−) m/z 336 (M−H)$^−$;

Anal. Calcd for $C_{16}H_{13}F_2NO_3S$: C, 56.96; H, 3.88; N, 4.15. Found: C, 57.01; H, 3.78; N, 4.08.

EXAMPLE 80

8-(4-Chloro-3-fluorophenyl)-2,3,4,5,6,8-hexahydro-7H-cyclopenta[b]thieno[2,3-e]pyridin-7-one, 1,1-dioxide 4-Chloro-3-fluorobenzaldehyde (180 mg, 1.13 mmol) was treated according to the procedure described in Example 56 to provide 135 mg of the title compound as a tan solid.

mp>260° C.

$^1$H NMR (DMSO-$d_6$) 2.30 (t, 2H), 2.50–2.75 (m, 2H), 2.87 (dt, 1H), 3.05 (dt, 1H), 3.40 (t, 2H), 4.73 (s, 1H), 7.10 (dd, 1H), 7.21 (dd, 1H), 7.45 (t, 1H), 10.32 (br s, 1H);

MS (APCI−) m/z 352 (M−H)$^−$;

Anal. Calcd for $C_{16}H_{13}ClFNO_3S$: C, 54.31; H, 3.70; N, 3.95. Found: C, 54.08; H, 3.65; N, 3.88.

EXAMPLE 81

9-(3-Chloro-4-fluorophenyl)-2,3,5,6,7,9-hexahydrothieno[3,2-b]quinolin-8(4H)-one, 1,1-dioxide 3-Chloro-4-fluorobenzaldehyde (264 mg, 1.66 mmol) was treated according to the procedure described in Example 43 to provide 317 mg of the title compound as a white solid.

mp>260° C.

$^1$H NMR (DMSO-$d_6$) 1.73–1.96 (m, 2H), 2.23 (m, 2H), 2.55 (m, 2H), 2.82 (dt, 1H), 3.02 (dt, 1H), 3.46 (m, 2H), 4.85 (s, 1H), 7.17 (m, 1H), 7.28 (m, 2H), 9.75 (br s, 1H);

MS (APCI−) m/z 366 (M−H)$^-$;

Anal. Calcd for $C_{17}H_{15}ClFNO_3S$: C, 55.51; H, 4.11; N, 3.80. Found: C, 55.24; H, 3.97; N, 3.85.

EXAMPLE 82

8-(3-Cyano-4-fluorophenyl)-2,3,4,5,6,8-hexahydrothieno[3,2-b:2i,3i-e]pyridine, 1,1,7,7-tetraoxide

EXAMPLE 82A

3-Cyano-4-fluorobenzyl bromide

A solution of 3-Cyano-4-fluorotoluene (1.0 g, 7.4 mmol), N-bromosuccinimide (1.3 g, 7.4 mmol) and catalytic 2,2i-azobisisobutyronitrile (AIBN) in benzene was heated to reflux for 16 hours, evaporated to dryness and flash chromatographed over silica gel eluting with 10% ethyl acetate/hexane to provide 1.0 g of 3-cyano-4-fluorobenzyl bromide.

$^1$H NMR (CDCl$_3$) d 4.45 (s, 2H), 7.21 (t, 1H), 7.65 (m, 2H).

EXAMPLE 82B

3-Cyano-4-fluorobenzyl alcohol

A solution of 85% formic acid (0.63 mL) and triethylamine (2.32 mL, 16.7 mmol) in acetonitrile at 0° C. was treated with the product from Example 82A (1.3 g, 5.6 mmol), stirred at room temperature for 3 hours, the reaction evaporated to dryness, partitioned between ethyl acetate/water, the organic layer dried with sodium sulfate, filtered and solvent evaporated to provide a crude formate ester. This residue was dissolved in methanol:water (5:1), treated with a catalytic amount of concentrated hydrochloric acid, stirred at room temperature overnight, evaporated to dryness, and flash chromatographed over silica gel eluting with ethyl acetate:hexane (1:1) to provide 0.40 g 3-cyano-4-fluorobenzyl alcohol.

$^1$H NMR (CDCl$_3$) d 1.81 (t, 1H), 4.72 (d, 2H), 7.21 (t, 1H), 7.62 (m, 2H).

EXAMPLE 82C

3-Cyano-4-fluorobenzaldehyde

A solution of the product from Example 82B (0.40 g, 2.6 mmol) in chloroform (50 mL) was treated with manganese dioxide (0.55 g, 7.8 mmol), stirred at room temperature overnight, filtered, solvent evaporated and the residue flash chromatographed over silica gel eluting with ethyl acetate-:hexane (1:1) to provide 0.21 g 3-cyano-4-fluorobenzaldehyde.

$^1$H NMR (CDCl$_3$) d 7.43 (t, 1H), 8.17 (m, 2H), 9.99 (s, 1H).

EXAMPLE 82D

3-Cyano-4-fluorobenzaldehyde (0.21 g, 1.4 mmol) was treated according to the procedure described in Example 62 to provide 0.20 g of the title compound as a tan solid.

mp 275–280° C. (dec);

$^1$H NMR (DMSO-$d_6$) 2.82 (m, 2H), 3.0 (m, 2H), 3.4 (m, 4H), 5.06 (s, 1H), 7.48 (t, 1H), 7.7 (m, 1H), 7.86 (dd, 1H) 10.1 (s, 1H);

MS (ESI+) m/z 398 (M+NH$_4$)$^+$, MS (ESI−) m/z 379 (M−H)$^-$;

Anal. Calcd for $C_{16}H_{13}FN_2O_4S_2$: C, 50.52; H, 3.44; N, 7.36. Found: C, 50.47; H, 3.52; N, 7.26.

EXAMPLE 83

(+)(9R)-9-(3-Bromo-4-fluorophenyl)-2,3,5,6,7,9-hexahydrothieno[3,2-b]quinolin-8(4H)-one, 1,1-dioxide The product from Example 43 (0.50 g) was chromatographed on a 5×25 cm Regis WhelkO 2 chiral column with 280 g of packing, eluting with hexane:methanol:methylene chloride (77.5/15/7.5) as the mobile phase with a flow rate of 117 mL/minute to provide 220 mg of the title compound as the more polar enantiomer.

[ ]$^{23}_D$+50.24° (CH$_3$CN);

$^1$H NMR (DMSO-$d_6$) 1.72–1.98 (m, 2H), 2.22 (m, 2H), 2.55 (m, 2H), 2.8 (m, 1H), 3.1 (m, 1H), 3.32 (m, 2H), 4.82 (s, 1H), 7.2 (m, 2H), 7.4 (m, 1H), 9.8 (s, 1H);

MS (APCI+) m/z 414 (M+H)$^+$;

Anal. Calcd for $C_{17}H_{15}BrFNO_3S$: C, 49.52; H, 3.66; N, 3.39. Found: C, 49.56; H, 3.86; N, 3.33.

EXAMPLE 84

(−)(9S)-9-(3-Bromo-4-fluorophenyl)-2,3,5,6,7,9-hexahydrothieno[3,2-b]quinolin-8(4H)-one, 1,1-dioxide From the chiral chromatography described in Example 83 was obtained 210 mg of the title compound as the less polar enantiomer.

[ ]$^{23}_D$−48.8 (CH$_3$CN);

$^1$H NMR (DMSO-$d_6$) 1.72–1.98 (m, 2H), 2.22 (m, 2H), 2.52 (m, 2H), 2.8 (m, 1H), 3.1 (m, 1H), 3.31 (m, 2H), 4.82 (s, 1H), 7.2 (m, 2H), 7.4 (m, 1H), 9.8 (s, 1H);

MS (APCI+) m/z 414 (M+H)$^+$;

Anal. Calcd for $C_{17}H_{15}BrFNO_3S$: C, 49.52; H, 3.66; N, 3.39. Found: C, 49.54; H, 3.76; N, 3.41.

EXAMPLE 85

8-(2,1,3-Benzoxadiazol-5-yl)-2,3,4,5,6,8-hexahydro-7H-cyclopenta[b]thieno[2,3-e]pyridin-7-one, 1,1-dioxide 2,1,3-Benzoxadiazole-5-carboxaldehyde (0.296 g, 2.00 mmol), prepared according to the method of Gasco (*Eur. J Med. Chem.* 1996, 31, 3), tetrahydrothiophene-3-oxo-1,1-dioxide (0.27 g, 2.0 mmol), and 3-amino-2-cyclopenten-1-one (0.194 g, 2.00 mmol) were heated in ethanol (4 mL) to 80° C. for 2 days in a sealed tube, treated with 1.0 M HCl in ether (1 mL), heated to reflux for 3 hours, cooled, the solid precipitate collected, washed with ethanol and dried to provide 0.27 g of the title compound.

$^1$H NMR (DMSO-$d_6$) 2.31 (t, 2H), 2.65 (m, 2H), 2.9 (m, 1H), 3.05 (m, 1H), 3.42 (m, 2H), 4.92 (s, 1H), 7.55 (d, 1H), 7.82 (s, 1H), 7.96 (d, 1H), 10.42 (s, 1H);

MS (CI/NH3) m/z 361 (M+NH$_4$)$^+$;

Anal. Calcd for C$_{16}$H$_{13}$N$_3$O$_4$S: C, 55.96; H, 3.81; N, 12.23. Found: C, 55.80; H, 3.73; N, 12.18.

EXAMPLE 86

(−)(8S)-8-(3-Bromo-4-fluorophenyl)-2,3,4,5,6,8-hexahydro-7H-cyclopenta[b]thieno[2,3-e]pyridin-7-one, 1,1-dioxide The product from Example 56 (0.80 g) was chromatographed on a 5×25 cm Regis WhelkO 2 chiral column with 280 g of packing, eluting with hexane:methanol:methylene chloride (70/15/15) as the mobile phase at a flow rate of 117 mL/minute to provide 250 mg of the title compound as the less polar enantiomer.

[ ]$^{23}_D$−4.5° (CH$_3$CN);

$^1$H NMR (DMSO-d$_6$) 2.3 (t, 2H), 2.63 (m, 2H), 2.85 (m, 1H), 3.06 (m, 1H), 3.4 (m, 2H), 4.71 (s, 1H), 7.25 (d, 2H), 7.47 (d, 1H) 10.35 (s, 1H);

MS (ESI+) m/z 400 (M+H)$^+$;

Anal. Calcd for C$_{16}$H$_{13}$BrFNO$_3$S: C, 48.25; H, 3.29; N, 3.52. Found: C, 48.14; H, 3.42; N, 3.42.

EXAMPLE 87

(+)(8R)-8-(3-Bromo-4-fluorophenyl)-2,3,4,5,6,8-hexahydro-7H-cyclopenta[b]thieno[2,3-e]pyridin-7-one, 1,1-dioxide From the chiral chromatography described in Example 86 was obtained 264 mg of the title compound as the more polar enantiomer.

[ ]$^{23}_D$+4.80° (CH$_3$CN);

$^1$H NMR (DMSO-d$_6$) 2.3 (m, 2H), 2.62 (m, 2H), 2.85 (m, 1H), 3.05 (m, 1H), 3.4 (m, 2H), 4.72 (s, 1H), 7.25 (m, 2H), 7.48 (d, 1H), 10.35 (s, 1H);

MS (ESI+) m/z 400 (M+H)$^+$;

Anal. Calcd for C$_{16}$H$_{13}$BrFNO$_3$S: C, 48.25; H, 3.29; N, 3.52. Found: C, 48.14; H, 3.52; N, 3.42.

EXAMPLE 88

9-(2,1,3-Benzoxadiazol-5-yl)-2,3,5,6,7,9-hexahydrothieno[3,2-b]quinolin-8(4H)-one, 1,1-dioxide 2,1,3-Benzoxadiazole-5-carboxaldehyde (0.296 g, 2.00 mmol) was treated according to the procedure described in Example 89 to provide 0.42 g of the title compound.

$^1$H NMR (DMSO-d$_6$) 1.9 (m, 2H), 2.25 (m, 2H), 2.55 (m, 2H), 2.88 (m, 1H), 3.05 (m, 1H), 3.4 (m, 2H), 5.0 (s, 1H), 7.51 (d, 1H), 7.7 (s, 1H), 7.95 (d, 1H), 9.96 (s, 1H);

MS (ESI+) m/z 358 (M+H)$^+$;

Anal. Calcd for C$_{17}$H$_{15}$N$_3$O$_4$S: C, 57.13; H, 4.23; N, 11.75. Found: C, 57.05; H, 4.31; N, 11.73.

EXAMPLE 89

9-(4-Fluoro-3-iodophenyl)-2,3,5,6,7,9-hexahydrothieno[3,2-b]quinolin-8(4H)-one, 1,1-dioxide

EXAMPLE 89A

3-Amino-4-fluorobenzyl alcohol

3-Amino-4-fluorobenzoic acid (15 g, 97 mmol) in THF at 0° C. was treated with 1.0 M BH$_3$.THF (50 mL), stirred overnight at room temperature, treated with an additional 130 mL 1.0 M BH$_3$.THF, stirred 10 hours, quenched by the addition of methanol, stirred 3 hours at room temperature, solvent evaporated, the product partitioned between aqueous sodium bicarbonate/methylene chloride, the organic layer dried (sodium sulfate), filtered and solvent evaporated. The product was purified by flash chromatography over silica gel (ethyl acetate/hexane 1:1) to provide 7.0 g of the title compound.

$^1$H NMR (CDCl$_3$) 4.58 (s, 2H), 6.67 (br m, 1H), 6.81 (d, 1H), 6.95 (t, 1H).

EXAMPLE 89B

4-Fluoro-3-iodobenzylalcohol

The product from Example 89A (7.0 g, 50 mmol) in water (100 mL) at 0° C. was treated slowly with concentrated sulfuric acid (30 mL) at a rate to maintain the temperature below 10° C., then treated dropwise with an aqueous solution of sodium nitrite (3.45 g, 50 mmol). This solution was then added to a solution of potassium iodide (8.13 g, 50 mmol) in water (15 mL), heated to 60° C. for 2 hours, cooled, extracted with methylene chloride, the organics washed with 10% sodium hydroxide, 1 M sodium thiosulfate, 10% hydrochloric acid, aqueous sodium bicarbonate, dried (sodium sulfate), filtered and solvent evaporated. The material was purified by flash chromatography over silica gel (ethyl acetate/hexane 7:3) to provide 6.4 g of the title compound.

$^1$H NMR (CDCl$_3$) 1.69 (t, 1H), 4.66 (d, 2H), 7.05 (t, 1H), 7.60 (d, 1H), 7.78 (dd, 1H).

EXAMPLE 89C

4-Fluoro-3-iodobenzaldehyde

The product from Example 89B (6.4 g, 26 mmol) in chloroform (300 mL) was treated with manganese dioxide (4.5 g, 50 mmol), stirred overnight, treated with an additional portion of manganese dioxide (2.25 g), stirred overnight, filtered and solvent evaporated. The material was purified by flash chromatography over silica gel (ethyl acetate/hexane 1:4) to provide 1.9 g of the title compound.

$^1$H NMR (CDCl$_3$) 7.23 (t, 1H), 7.89 (m, 1H), 8.32 (dd, 1H), 9.91 (s, 1H).

EXAMPLE 89D 9-(4-Fluoro-3-iodophenyl)-2,3,5,6,7,9-hexahydrothieno[3.2-b]quinolin-8(4H)-one, 1,1-dioxide 4-Fluoro-3-iodobenzaldehyde (0.25 g, 1.0 mmol), tetrahydrothiophene-3-oxo-1,1-dioxide (0.13 g, 1.0 mmol), 3-amino-2-cyclohexen-1-one (0.11 g, 1.0 mmol) and triethylamine (0.07 mL) were heated in ethanol (2 mL) to 80° C. in a sealed tube for 96 hours, cooled, solvent evaporated, flash chromatographed on silica gel (10% ethanol/methylene chloride), the product dissolved in ethanol, treated with 1.0 M HCl in ether (1 mL), heated to reflux for 2 hours, cooled, the solid precipitate collected, washed with ethanol and dried to provide 0.20 g of the title compound.

mp>250° C.;

$^1$H NMR (DMSO-d$_6$) 1.88 (m, 2H), 2.22 (m, 2H), 2.62 (m, 2H), 2.7 (m, 1H), 3.02 (m, 1H), 3.45 (m, 2H), 4.81 (s, 1H), 7.12 (m, 1H), 7.18 (m, 1H), 7.55 (dd, 1H), 9.81 (s, 1H);

MS (ESI+) m/z 460 (M+H)$^+$;

Anal. Calcd for $C_{17}H_{15}FINO_3S$: C, 44.45; H, 3.29; N, 3.04. Found: C, 44.51; H, 3.31; N, 2.97.

EXAMPLE 90

8-(4-Fluoro-3-iodophenyl)-2,3,4,5,6,8-hexahydro-7H-cyclopenta[b]thieno[2,3-e]pyridin-7-one, 1,1-dioxide 4-Fluoro-3-iodobenzaldehyde (0.25 g, 1.0 mmol), tetrahydrothiophene-3-oxo-1,1-dioxide (0.13 g, 1.0 mmol) and 3-amino-2-cyclopenten-1-one (97 mg, 1.0 mmol) were heated in ethanol (2 mL) to 80° C. in a sealed tube for 96 hours, cooled, solvent evaporated, flash chromatographed on silica gel (10% ethanol/methylene chloride), the product dissolved in ethanol, treated with 1.0 M HCl in ether (1 mL), heated to reflux for 2 hours, cooled, the solid precipitate collected, washed with ethanol and dried to provide 0.10 g of the title compound.

mp>250° C.;

$^1$H NMR (DMSO-$d_6$) 2.3 (t, 2H), 2.62 (m, 2H), 2.85 (m, 1H), 3.08 (m, 1H), 3.4 (m, 2H), 4.68 (s, 1H), 7.13 (t, 1H), 7.24 (m, 1H), 7.6 (dd, 1H), 10.33 (s, 1H);

MS (ESI+) m/z 446 (M+H)$^+$;

Anal. Calcd for $C_{16}H_{13}FINO_3S$: C, 43.16; H, 2.94; N, 3.14. Found: C, 42.91; H, 2.94; N, 3.00.

EXAMPLE 91

(+)9-(3-Bromo-4-fluorophenyl)-3,4,5,6,7,9-hexahydrocyclopenta[b]thiopyrano[2,3-e]pyridin-8(2H)-one, 1,1-dioxide The product from Example 40 (1.476 g, 3.58 mmol) as a slurry in THF (20 mL) under nitrogen at 5° C. was treated dropwise with a solution of 1.0 M potassium tert-butoxide in THF (3.9 mL), allowed to warm to room temperature over 20 minutes, treated with a solution of (−)-8-phenylmenthylchloroformate (1.17 g, 3.97 mmol) in THF (5 mL), stirred at room temperature overnight, quenched in aqueous sodium bicarbonate, extracted with diethyl ether (2×), the organics dried with sodium sulfate, filtered and solvent evaporated to provide a mixture of diastereomeric carbamates. This mixture was flash chromatographed over a 6×36 cm column of silica gel, eluting with ether:hexane (85/15) to provide 746 mg of the less polar diastereomer. This material, as a slurry in methanol (10 mL) under nitrogen, was treated with catalytic sodium methoxide, stirred at room temperature for 24 hours, treated with glacial acetic acid (3 drops), the solid precipitate collected, washed with ethyl alcohol and dried to provide 227 mg of the title compound as a white solid.

[ ]$^{23}_D$+63.9 (MeCN);

$^1$H NMR (DMSO-$d_6$) 2.15–2.35 (m, 4H), 2.46–2.70 (m, 4H), 3.23 (m, 2H), 4.83 (s, 1H), 7.25 (m, 2H), 7.42 (dd, 1H), 9.96 (br s, 1H);

MS (APCI−) m/z 410 (M−H)$^-$;

Anal. Calcd for $C_{17}H_{15}BrFNO_3S$: C, 49.53; H, 3.67; N, 3.40. Found: C, 49.47; H, 3.53; N, 3.37.

EXAMPLE 92

(−)9-(3-Bromo-4-fluorophenyl)-3,4,5,6,7,9-hexahydrocyclopenta[b]thiopyrano[2,3-e]pyridin-8(2H)-one, 1,1-dioxide From the chromatography of diastereomers described in Example 91 was obtained 824 mg of the impure more polar diastereomer. This material was flash chromatographed over a 6×36 cm column of silica gel, eluting with ether:hexane (9/1) to provide 695 mg of the more polar diastereomer. This diastereomer, as a slurry in methanol (10 mL) under nitrogen, was treated with catalytic sodium methoxide, stirred at room temperature for 5 days, treated with glacial acetic acid (3 drops), the solid precipitate collected, washed with ethyl alcohol and dried to provide 120 mg of the title compound as a white solid. The filtrate was flash chromatographed (5–15% ethanol/methylene chloride) and the product triturated with ethyl acetate to provide an additional 186 mg of the title compound.

[ ]$^{23}_D$−60.8 (MeCN)

$^1$H NMR (DMSO-$d_6$) 2.15–2.30 (m, 4H), 2.47–2.70 (m, 4H), 3.20 (m, 2H), 4.83 (s, 1H), 7.25 (m, 2H), 7.41 (dd, 1H), 9.96 (br s, 1H);

MS (APCI−) m/z 410 (M−H)$^-$;

Anal. Calcd for $C_{17}H_{15}BrFNO_3S$: C, 49.53; H, 3.67; N, 3.40. Found: C, 49.61; H, 3.58; N, 3.34.

EXAMPLE 93

(+)10-(3-Bromo-4-fluorophenyl)-3,4,6,7,8,10-hexahydro-2H-thiopyrano[3,2-b]quinolin-9(5H)-one, 1,1-dioxide The product from Example 4 (1.646 g, 3.86 mmol) was processed by the method described in Example 91 to provide 223 mg of the title compound as a white solid.

[ ]$^{23}_D$+7.3 (DMSO);

$^1$H NMR (DMSO-$d_6$) 1.75 (m, 1H), 1.88 (m, 1H), 2.20 (m, 4H), 2.50 (m, 4H), 3.20 (m, 2H), 5.01 (s, 1H), 7.15–7.28 (m, 2H), 7.88 (dd, 1H), 9.39 (br s, 1H);

MS (APCI−) m/z 424 (M−H)$^-$;

Anal. Calcd for $C_{18}H_{17}BrFNO_3S$: C, 50.71; H, 4.02; N, 3.29. Found: C, 50.73; H, 4.24; N, 3.26.

EXAMPLE 94

(−)10-(3-Bromo-4-fluorophenyl)-3,4,6,7,8,10-hexahydro-2H-thiopyrano[3,2-b]quinolin-9(5H)-one, 1,1-dioxide The product from Example 4 (1.646 g, 3.86 mmol) was processed by the methods described in Example 91 and Example 92 to provide 148 mg of the title compound as a white solid.

[ ]$^{23}_D$−5.2 (DMSO);

$^1$H NMR (DMSO-$d_6$) 1.73 (m, 1H), 1.88 (m, 1H), 2.20 (m, 4H), 2.50 (m, 4H), 3.20 (m, 2H), 5.01 (s, 1H), 7.15–7.27 (m, 2H), 7.38 (dd, 1H), 9.40 (br s, 1H);

MS (APCI−) m/z 424 (M−H)$^-$;

Anal. Calcd for $C_{18}H_{17}BrFNO_3S$: C, 50.71; H, 4.02; N, 3.29. Found: C, 50.68; H, 4.17; N, 3.22.

EXAMPLE 95

(+)(9R)-9-(3,4-Dichlorophenyl)-3,4,5,6,7,9-hexahydrothieno[3,2-b]quinolin-8(2H)-one, 1,1-dioxide The title compound from Example 29 (1.65 g, 4.30 mmol) as a slurry in THF (20 mL) under nitrogen at 5° C. was treated dropwise with a solution of 1.0 M potassium tert-butoxide in THF (3.9 mL), allowed to warm to room temperature over 20 minutes, treated with a solution of (−)-8-phenylmenthylchloroformate (4.3 mmol) in THF (5 mL), stirred at room temperature overnight, quenched in aqueous sodium bicarbonate, extracted with diethyl ether (3x), the organics dried with sodium sulfate, filtered and solvent evaporated to provide a mixture of diastereomeric carbamates. This mixture was flash chromatographed over a 6x40 cm column of silica gel, eluting with chloroform:hexane:ether (7:2:1) to provide 664 mg of the less polar diastereomer. This material, as a slurry in methanol (10 mL) under nitrogen, was treated with catalytic sodium methoxide, stirred at room temperature overnight, treated with glacial acetic acid (2 drops), the solid precipitate collected, washed with ethyl alcohol and dried to provide 295 mg of the title compound as a white solid.

$[\ ]^{23}_D$+70.90 (DMSO);

$^1$H NMR (DMSO-$d_6$) 1.75–1.95 (m, 2H), 2.23 (m, 2H), 2.54 (m, 2H), 2.83 (dt, 1H), 3.02 (dt, 1H), 3.45 (m, 2H), 4.84 (s, 1H), 7.16 (dd, 1H), 7.34 (d, 1H), 7.49 (d, 1H), 9.82 (br s, 1H);

MS (APCI–) m/z 382 (M–H)$^-$;

Anal. Calcd for $C_{17}H_{15}Cl_2NO_3S$: C, 53.14; H, 3.93; N, 3.64. Found: C, 53.38; H, 4.19; N, 3.61.

EXAMPLE 96

(−)(9S)-9-(3,4-Dichlorophenyl)-3,4,5,6,7,9-hexahydrothieno[3,2-b]quinolin-8(2H)-one, 1,1-dioxide From the chromatography of the diastereomers described in Example 95 was obtained the impure more polar diastereomer. This material was flash chromatographed over a 6x40 cm column of silica gel, eluting with chloroform:hexane:ether (7:2:1) to provide 628 mg of the more polar diastereomer. This diastereomer, as a slurry in methanol (10 mL) under nitrogen, was treated with catalytic sodium methoxide, stirred at room temperature overnight, treated with glacial acetic acid (2 drops), the solid precipitate collected, washed with ethyl alcohol and dried to provide 228 mg of the title compound as a white solid.

$[\ ]^{23}_D$−68.8° (DMSO);

$^1$H NMR (DMSO-$d_6$) 1.75–1.95 (m, 2H), 2.23 (m, 2H), 2.55 (m, 2H), 2.73 (dt, 1H), 3.03 (dt, 1H), 3.35 (m, 2H), 4.84 (s, 1H), 7.17 (dd, 1H), 7.35 (d, 1H), 7.50 (d, 1H), 985 (br s, 1H);

MS (APCI–) m/z 382 (M–H)$^-$;

Anal. Calcd for $C_{17}H_{15}Cl_2NO_3S$: C, 53.14; H, 3.93; N, 3.64. Found: C, 53.11; H, 4.01; N, 3.59.

EXAMPLE 97

(+)(9R)-9-(2,1,3-Benzoxadiazol-5-yl)-2,3,5,6,7,9-hexahydrothieno[3,2-b]quinolin-8(4H)-one, 1,1-dioxide The product from Example 88 (1.34 g) was processed using the method described in Example 95 to provide 120 mg of the title compound as a white solid.

$[\ ]^{23}_D$+43.3° (DMSO);

$^1$H NMR (DMSO-$d_6$) 1.9 (m, 2H), 2.23 (m, 2H), 2.56 (m, 2H), 2.88 (m, 1H), 3.05 (m, 1H), 3.4 (m, 2H), 5.0 (s, 1H), 7.51 (d, 1H), 7.7 (s, 1H), 7.95 (d, 1H), 9.95 (s, 1H);

MS (ESI–) m/z 356 (M–H)$^-$;

Anal. Calcd for $C_{17}H_{15}N_3O_4S$: C, 57.13; H, 4.23; N, 11.75. Found: C, 56.98; H, 4.28; N, 11.76.

EXAMPLE 98

(−)(9S)-9-(2,1,3-Benzoxadiazol-5-yl)-2,3,5,7,9-hexahydrothieno[3,2-b]quinolin-8(4H)-one, 1,1-dioxide The product from Example 88 (1.34 g) was processed using the methods of Examples 95 and 96 to provide 110 mg of the title compound as a white solid.

$[\ ]^{23}_D$−41.7° (DMSO);

$^1$H NMR (DMSO-$d_6$) 1.9 (m, 2H), 2.25 (m, 2H), 2.57 (m, 2H), 2.9 (m, 1H), 3.05 (m, 1H), 3.4 (m, 2H), 5.0 (s, 1H), 7.51 (d, 1H), 7.7 (s, 1H), 7.95 (d, 1H), 9.95 (s, 1H);

MS (ESI–) m/z 356 (M–H)$^-$;

Anal. Calcd for $C_{17}H_{15}N_3O_4S$: C, 57.13; H, 4.23; N, 11.75. Found: C, 56.97; H, 4.43; N, 11.71.

EXAMPLE 99

(+)(9R)-9-(4-Chloro-3-nitrophenyl)-3,4,5,6,7,9-hexahydrothieno[3,2-b]quinolin-8(2H)-one, 1,1-dioxide The product from Example 34 (1.64 g) was processed according to the method described in Example 95 to provide 300 mg of the title compound.

$[\ ]^{23}_D$+41.040 (DMSO);

$^1$H NMR (DMSO-$d_6$) 1.90 (m, 2H), 2.25 (m, 2H), 2.52 (m, 2H), 2.85 (m, 1H), 3.02 (m, 1H), 3.35 (m, 2H), 4.95 (s, 1H), 7.54 (dd, 1H, J=3 Hz), 7.65 (d, 1H, J=9 Hz), 780 (d, 1H, J=3 Hz), 9.90 (s, 1H);

MS (ESI–) m/z 393 (M–H)$^-$;

Anal. Calcd for $C_{17}H_{15}ClN_2O_5S$: C, 51.71; H, 3,83; N, 7.10. Found: C, 51.72; H, 3.85; N, 7.10.

EXAMPLE 100

(−)(9S)-9-(4-Chloro-3-nitrophenyl)-3,4,5,6,7,9-hexahydrothieno[3,2-b]quinolin-8(2H)-one, 1,1-dioxide The product from Example 34 (1.64 g) was processed using the methods described in Examples 95 and 96 to provide 424 mg of the title compound as a white solid.

$[\ ]^{23}_D$−31.74° (DMSO);

$^1$H NMR (DMSO-$d_6$) 1.92 (m, 2H), 2.24 (m, 2H), 2.52 (m, 2H), 2.86 (m, 1H), 3.02 (m, 1H), 3.38 (m, 2H), 4.95 (s, 1H), 7.54 (dd, 1H, J=3 Hz), 7.66 (d, 1H, J=9 Hz), 7.79 (d, 1H, J=3 Hz), 9.89 (s, 1H);

MS (ESI–) m/z 393 (M–H)$^-$;

Anal. Calcd for $C_{17}H_{15}ClN_2O_5S$: C, 7.10; H, 3.83; N, 7.10. Found: C, 51.70; H, 3.83; N, 7.08.

EXAMPLE 101

11-(3-Bromo-4-fluorophenyl)-2,34,5,7,8,9,11-octahydrothiepino[3,2-b]quinolin-10(6H)-one, 1,1-dioxide A solution of 3-bromo-4-fluorobenzaldehyde (1.22 g, 6.00 mmol), 3-amino-2-cyclohexen-1-one (667 mg, 6.00 mmol) and thiacycloheptan-3-one 1,1-dioxide (973 mg, 6.00 mmol) (prepared according to the method described in J. Heterocycl. Chem. (1990), 27, 1453) in ethyl alcohol (10 mL) with triethylamine (0.4 mL) was heated to 80° C. in a sealed tube for 3 days, cooled, the solid precipitate collected, washed with ethyl alcohol and dried to provide 1.8 g of the title compound as a white solid.

$^1$H NMR (DMSO-$d_6$) 1.65 (m, 1H), 1.75 (m, 2H), 1.90 (m, 1H), 2.02 (m, 2H), 2.52 (m, 2H), 2.75 (m, 3H), 3.15 (m, 1H), 4.95 (s, 1H), 7.20 (m, 1H), 7.25 (m, 1H), 7.40 (dd, 1H, J=3 Hz), 9.44 (s, 1H);

MS (ESI+) m/z 441 (M+H)$^+$;

Anal. Calcd for $C_{19}H_{19}BrFNO_3S$: C, 51.83; H, 4.35; N, 3.18. Found: C, 51.59; H, 4.35; N, 3.18.

EXAMPLE 102

10-(3-Bromo-4-fluorophenyl)-2,3,4,5,6,7,8,10-octahydro-9H-cyclopenta[b]thiepino[2,3-e]pyridin-9-one A solution of 3-bromo-4-fluorobenzaldehyde (639 mg, 3.14 mmol), 3-amino-2-cyclopenten-1-one (305 mg, 3.14 mmol) and thiacycloheptan-3-one 1,1-dioxide (510 mg, 3.14 mmol) in ethyl alcohol (10 mL) was heated to 80° C. in a sealed tube for 3 days, cooled, the solid precipitate collected, washed with ethyl alcohol and dried to provide 700 mg of the title compound as a white solid.

mp 210° C.;

$^1$H NMR (DMSO-d$_6$) 1.60 (m, 1H), 1.82 (m, 1H), 2.05 (m, 2H), 2.32 (m, 2H), 2.62 (m, 3H), 2.92 (m, 2H), 3.20 (m, 1H), 4.75 (s, 1H), 7.25 (dd, 1H, J=3 Hz), 7.32 (m, 1H), 7.45 (dd, 1H, J=3 Hz), 10.02 (s, 1H);

MS (ESI+) m/z 427 (M+H)$^+$;

Anal. Calcd for $C_{18}H_{17}BrFNO_3S$: C, 50.71; H, 4.02; N, 3.29. Found: C, 50.71; H, 4.10; N, 3.20.

Determination of Potassium Channel Opening Activity Membrane Hyperpolarization Assays Compounds were evaluated for potassium channel opening activity using the rat thoracic aorta smooth muscle A10 cell line or primary cultured guinea-pig urinary bladder (GPB) cells.

The A10 cell line was purchased from the American Type Culture Collection (Rockville, Md.; Cat # 30-2002). Cells were grown in 96-well clear-bottomed black plates (Packard) in culture media (composition: Dulbecco's modified Eagle's medium supplemented with 20% Fetal Bovine Serum, 100 units/mL penicillin, 100 units/mL streptomycin and 0.25 mg/mL amphotericin B) at 37° C. with 5% $CO_2$ in a humidified chamber to form a confluent monolayer.

For the preparation of urinary bladder smooth muscle cells, urinary bladders were removed from male guinea-pigs (Hartley, Charles River, Wilmington, Mass.) weighing 300–400 g and placed in ice-cold $Ca^{2+}$-free Krebs solution (Composition, mM: KCl, 2.7; $KH_2PO_4$, 1.5; NaCl, 75; $Na_2HPO_4$, 9.6; $Na_2HPO_4 \cdot 7H_2O$, 8; $MgSO_4$, 2; glucose, 5; HEPES, 10; pH 7.4). Cells were isolated by enzymatic dissociation as previously described with minor modifications (Klockner, U. and Isenberg, G., Pflugers Arch. 1985, 405, 329–339). The bladder was cut into small sections and incubated in 5 mL of the Kreb's solution containing 1 mg/mL collagenase (Sigma, St. Louis, Mo.) and 0.2 mg/mL pronase (Calbiochem, La Jolla, Calif.) with continuous stirring in a cell incubator for 30 minutes. The mixture was then centrifuged at 1300× g for 5 minutes, and the pellet resuspended in Dulbecco's PBS (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media. Cells were plated in clear-bottomed black 96-well plates (Packard) for membrane potential studies at a density of 20,000 cells/well and maintained in a cell incubator with 90% air: 10% $CO_2$ until confluent. Cells were confirmed to be of smooth muscle type by cytoskeletal staining using a monoclonal mouse anti human—smooth muscle actin (Biomeda, Foster City, Calif.).

Functional activity at potassium channels was measured by evaluating changes in membrane potential using the bis-oxonol dye DiBAC(4)$_3$ (Molecular Probes) in a 96-well cell-based kinetic assay system, Fluorescent Imaging Plate Reader (FLIPR) (K. S. Schroeder et al., J. Biomed. Screen., v. 1 pp. 75–81 (1996)). DiBAC(4)$_3$ is an anionic potentiometric probe which partitions between cells and extracellular solution in a membrane potential-dependent manner. With increasing membrane potential (for example, $K^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent smooth muscle A10 or guinea-pig urinary bladder cells cultured in black clear-bottomed 96-well plates were rinsed twice with 200 mL assay buffer (composition, mM: HEPES, 20; NaCl, 120; KCl, 2; $CaCl_2$, 2; $MgCl_2$, 1; glucose, 5; pH 7.4 at 25° C.) containing 5 M DiBAC(4)$_3$ and incubated with 180 mL of the buffer in a cell incubator for 30 minutes at 37° C. to ensure dye distribution across the membrane. After recording the baseline fluorescence for 5 minutes, the reference or test compounds, prepared at 10 times concentration in the assay buffer, were added directly to the wells. Changes in fluorescence were monitored for an additional 25 minutes. Hyperpolarization responses were corrected for any background noise and were normalized to the response observed with 10 M of the reference compound P1075 (assigned as 100%), a potent opener of smooth muscle $K_{ATP}$ channels (Quast et al., Mol. Pharmacol., v. 43 pp. 474–481 (1993)).

Routinely, five concentrations of P1075 or test compounds (log or half-log dilutions) were evaluated and the maximal steady-state hyperpolarization values (expressed as % relative to P1075) plotted as a function of concentration. The $EC_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate.

TABLE 1

Membrane Hyperpolarization (MHP) in A10 and Guinea-Pig Bladder (GPB) Cells

| | MHP in A10 Cells | | MHP in GPB Cells | |
|---|---|---|---|---|
| Example # | Maximal Response (% P1075) | EC50(M) | Maximal Response (% P1075) | EC50(M) |
| 1 | 93 | 2.1 | 80 | 1.4 |
| 2 | 73 | 0.70 | 77 | 2.1 |
| 3 | 90 | 1.6 | 110 | 1.3 |
| 4 | 110 | 0.50 | 120 | 0.38 |
| 5 | 78 | 5.5 | 41 | 18 |
| 6 | 48 | 12 | 31 | 17 |
| 7 | 94 | 4.8 | 100 | 2.8 |
| 8 | 66 | 7.5 | 100 | 2.5 |
| 9 | 39 | 16 | 67 | 7.2 |
| 10 | 61 | 4.5 | 100 | 15 |
| 11 | 42 | 11 | 29 | 20 |

TABLE 1-continued

Membrane Hyperpolarization (MHP) in A10 and Guinea-Pig Bladder (GPB) Cells

| Example # | MHP in A10 Cells | | MHP in GPB Cells | |
|---|---|---|---|---|
| | Maximal Response (% P1075) | EC50(M) | Maximal Response (% P1075) | EC50(M) |
| 12 | 34 | >10 | 16 | >10 |
| 13 | 110 | 2.0 | 100 | 1.6 |
| 14 | 83 | 5.2 | 100 | 1.8 |
| 15 | 74 | 5.7 | 95 | 2.0 |
| 16 | 83 | 6.3 | 47 | 3.5 |
| 17 | 79 | 4.2 | 73 | 5.1 |
| 18 | 64 | 7.6 | 66 | 1.4 |
| 19 | 100 | 0.39 | 120 | 0.43 |
| 20 | 52 | 10 | 76 | 3.0 |
| 21 | 33 | >10 | 15 | >10 |
| 22 | 15 | >10 | 71 | 3.6 |
| 23 | 49 | 3.6 | 91 | 3.0 |
| 24 | 76 | 3.9 | 100 | 1.4 |
| 25 | 90 | 1.8 | 110 | 0.84 |
| 26 | 42 | 4.4 | 93 | 3.2 |
| 27 | 40 | 3.7 | 75 | 3.0 |
| 28 | 42 | 3.6 | 78 | 2.9 |
| 29 | 110 | 0.24 | 120 | 0.46 |
| 30 | 91 | 3.8 | 97 | 2.3 |
| 31 | 100 | 0.27 | 100 | 0.16 |
| 32 | 100 | 0.64 | 110 | 0.44 |
| 33 | 100 | 3.0 | 100 | 2.0 |
| 34 | 97 | 0.28 | 110 | 0.53 |
| 35 | 93 | 2.4 | 91 | 1.1 |
| 36 | 96 | 1.7 | 110 | 0.48 |
| 37 | 100 | 0.15 | 110 | 0.20 |
| 38 | 100 | 0.51 | 140 | 0.44 |
| 39 | 120 | 0.35 | 120 | 0.17 |
| 40 | 120 | 0.23 | 130 | 0.15 |
| 41 | 120 | 1.0 | 120 | 0.62 |
| 42 | 57 | 3.7 | 69 | 3.9 |
| 43 | | | | |
| 44 | 100 | 0.28 | 120 | 0.15 |
| 45 | 77 | 3.8 | 92 | 2.4 |
| 48 | | | 100 | 0.13 |
| 49 | | | 92 | 0.56 |
| 50 | | | 87 | 1.4 |
| 51 | | | 102 | 0.93 |
| 52 | | | 79 | 4.3 |
| 53 | | | 103 | 0.40 |
| 54 | | | 107 | 3.2 |
| 55 | | | 103 | 2.6 |
| 54 | | | 133 | 0.11 |
| 57 | | | 104 | 0.12 |
| 58 | | | 124 | 0.37 |
| 59 | | | 0 | 0 |
| 60 | | | 117 | 0.076 |
| 61 | | | 101 | 0.059 |
| 62 | | | 0 | 0 |
| 63 | | | 50 | 3.2 |
| 64 | | | 88 | 0.39 |
| 65 | | | 96 | 0.24 |
| 66 | | | 90 | 0.21 |
| 67 | | | 84 | 0.74 |
| 68 | | | 99 | 1.9 |
| 69 | | | 99 | 0.24 |
| 70 | | | 93 | 0.15 |
| 71 | | | 57 | 5.4 |
| 72 | | | 97 | 0.042 |
| 73 | | | 102 | 2.7 |
| 74 | | | 90 | 0.52 |
| 75 | | | 79 | 1.7 |
| 76 | | | 67 | 1.8 |
| 77 | | | 109 | 0.22 |
| 78 | | | 111 | 2.7 |
| 79 | | | 116 | 0.73 |
| 80 | | | 108 | 0.52 |
| 81 | | | 110 | 0.078 |
| 82 | | | 63 | 6.5 |
| 83 | | | 91 | 0.063 |
| 84 | | | 95 | 0.11 |
| 85 | | | 79 | 0.83 |
| 86 | | | 85 | 1.1 |
| 87 | | | 93 | 0.044 |
| 88 | | | 90 | 0.38 |
| 89 | | | 79 | 0.060 |
| 90 | | | 83 | 0.028 |
| 91 | | | 44 | 15 |
| 92 | | | 93 | 0.052 |
| 93 | | | 114 | 1.21 |
| 94 | | | 86 | 0.058 |
| 97 | | | 86 | 0.216 |
| 98 | | | 96 | 0.215 |
| 102 | | | 84 | 2.3 |

In vitro Functional models

Compounds were evaluated for functional potassium channel opening activity using tissue strips obtained from Landrace pig bladders and human bladders.

Landrace pig bladders were obtained from female Landrace pigs of 9–30 kg. Landrace pigs were euthanized with an intraperitoneal injection of pentobarbital solution, Somlethal®, J.A. Webster Inc., Sterling Mass. The entire bladder was removed and immediately placed into Krebs Ringer bicarbonate solution (composition, mM: NaCl, 120; $NaHCO_3$, 20; dextrose, 11; KCl, 4.7; $CaCl_2$, 2.5; $MgSO_4$, 1.5; $KH_2PO_4$, 1.2; $K_2EDTA$, 0.01, equilibrated with 5% $CO_2$/95% $O_2$ pH 7.4 at 37° C.). Propranolol (0.004 mM) was included in all the assays to block adrenoceptors. The trigonal and dome portions were discarded. Strips 3–5 mm wide and 20 mm long were prepared from the remaining tissue cut in a circular fashion. The mucosal layer was removed. One end was fixed to a stationary glass rod and the other to a Grass FT03 transducer at a basal preload of 1.0 gram. Two parallel platinum electrodes were included in the stationary glass rod to provide field stimulation of 0.05 Hz, 0.5 milli-seconds at 20 volts. This low frequency stimulation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of $10^{-9}$ to $10^{-5}$ M using ½ log increments. After a 60 minute rinsing period, a concentration response curve (cumulative) was generated for the test agonist in the same fashion as that used for the control agonist P1075. The maximal efficacy of each compounds (expressed as % relative to P1075) is reported. The amount of agent necessary to cause 50% of the agents's maximal response ($ED_{50}$) was calculated using "ALLFIT" (DeLean et al., *Am. J. Physiol.*, 235, E97 (1980)), and agonist potencies were expressed as $pD_2$ (the negative logarithm). Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

Human bladders were obtained from women greater than 45 years old. The human tissue was obtained from the Anatomic Gift Foundation, Phoenix Ariz. Human tissue was received via overnight delivery on wet ice placed into Krebs Ringer bicarbonate solution (composition, mM: NaCl, 120; NaHCO$_3$, 20; dextrose, 11; KCl, 4.7; CaCl$_2$, 2.5; MgSO$_4$, 1.5; KH$_2$PO$_4$, 1.2; K$_2$EDTA, 0.01, equilibrated with 5% CO$_2$/95% O$_2$ pH 7.4 at 37° C.). Propranolol (0.004 mM) was included in all of the assays to block adrenoceptors. The trigonal and dome portions were discarded. Strips 3–5 mm wide and 20 mm long were prepared from the remaining tissue cut in a circular fashion. The mucosal layer was removed. For the human detrusor strips the tissues were contracted with 25 mM KCl which produced a steady state tension of approximately 400 centigrams. A control concentration response curve (cumulative) was generated for each tissue using the potassium channel opener P1075 as the control agonist. P1075 produced complete relaxation with concentrations from $10^{-9}$ to $10^{-4}$ M using ½ log increments. After a 60 minute rinsing period, a concentration response curve (cumulative) was generated for the test agonist in the same fashion as that used for the control agonist P1075. The maximal efficacies of the compounds (expressed as % relative to P1075) are reported. The amount of agent necessary to cause 50% of the agents's maximal response (ED$_{50}$) was calculated using "ALLFIT" (DeLean et al., *Am. J. Physiol.* 235, E97 (1980)), and agonist potencies were expressed as pD$_2$ (the negative logarithm). Agonist potencies were also expressed as an index relative to P1075. The index was calculated by dividing the ED$_{50}$ for P1075 by the ED$_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Strips

| Example # | Landrace Pig Bladder | | | Human Bladder | | |
|---|---|---|---|---|---|---|
| | Efficacy (% P1075) | pD2 | Index | Efficacy (% P1075) | pD2 | Index |
| 19 | 94 | 6.0 | 0.13 | 100 | 5.8 | 0.15 |
| 2 | 96 | 6.2 | 0.15 | | | |
| 1 | 100 | 5.5 | 0.022 | | | |
| 16 | 100 | 5.0 | 0.011 | | | |
| 11 | 100 | 4.1 | 0.0021 | | | |
| 5 | 96 | 4.8 | 0.0076 | | | |
| 3 | 85 | 6.0 | 0.11 | | | |
| 8 | 95 | 5.0 | 0.025 | | | |
| 4 | 93 | 6.2 | 0.18 | | | |
| 36 | 97 | 5.5 | 0.040 | | | |
| 26 | 78 | 4.5 | 0.0099 | | | |
| 25 | 88 | 5.4 | 0.038 | | | |
| 23 | 81 | 4.4 | 0.0053 | | | |
| 22 | 77 | 4.5 | 0.0069 | | | |
| 34 | 100 | 6.8 | 0.32 | | | |
| 38 | 98 | 6.2 | 0.14 | | | |
| 40 | 98 | 6.9 | 0.46 | | | |
| 30 | 99 | 5.5 | 0.018 | | | |
| 44 | 99 | 6.2 | 0.15 | | | |
| 43 | 98 | 6.6 | 0.41 | | | |
| 51 | 99 | 5.4 | 0.021 | | | |
| 52 | 100 | 5.6 | 0.018 | | | |
| 53 | 100 | 6.6 | 0.17 | | | |
| 54 | 89 | 4.9 | 0.015 | | | |
| 56 | 91 | 7.1 | 0.88 | | | |
| 57 | 100 | 6.8 | 0.42 | | | |
| 58 | 94 | 5.3 | 0.026 | | | |
| 60 | 100 | 6.9 | 0.60 | | | |

TABLE 2-continued

Functional Potassium Channel Opening Activity in Isolated Bladder Strips

| Example # | Landrace Pig Bladder | | | Human Bladder | | |
|---|---|---|---|---|---|---|
| | Efficacy (% P1075) | pD2 | Index | Efficacy (% P1075) | pD2 | Index |
| 61 | 100 | 7.1 | 0.71 | | | |
| 65 | 100 | 6.0 | 0.048 | | | |
| 66 | 94 | 6.3 | 0.12 | | | |
| 69 | 98 | 6.2 | 0.15 | | | |
| 70 | 100 | 6.3 | 0.15 | | | |
| 72 | 97 | 6.6 | 0.53 | | | |
| 73 | 98 | 4.4 | 0.0022 | | | |
| 74 | 100 | 6.1 | 0.081 | | | |
| 77 | 93 | 5.5 | 0.046 | | | |
| 81 | 91 | 6.4 | 0.39 | | | |
| 83 | 100 | 7.0 | 0.57 | | | |
| 84 | 100 | 6.8 | 0.69 | | | |
| 86 | 100 | 6.5 | 0.069 | | | |
| 87 | 100 | 7.5 | 0.90 | | | |
| 91 | 95 | 4.6 | 0.0034 | | | |
| 92 | 100 | 6.5 | 0.44 | | | |

As shown by the data in Tables 1 and 2, the compounds of this invention reduce stimulated contractions of the bladder by opening potassium channels and therefore have utility in the treatment of diseases prevented by or ameliorated with potassium channel openers.

The present invention also provides pharmaceutical compositions which comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other animals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound is mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology,* Volume XIV, Academic Press, New York, N.Y. (1976), p. 33 et seq.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camnphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenylethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetraethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The compounds of the invention, including but not limited to those specified in the examples, possess potassium channel opening activity in mammals (especially humans). As potassium channel openers, the compounds of the present invention are useful for the treatment and prevention of diseases such as asthma, epilepsy, hypertension, Raynaud's syndrome, impotence, migraine, pain, eating disorders, urinary incontinence, functional bowel disorders, neurodegeneration and stroke.

The ability of the compounds of the invention to treat asthma, epilepsy, hypertension, Raynaud's syndrome, impotence, migraine, pain, eating disorders, urinary incontinence, functional bowel disorders, neurodegeneration and stroke can be demonstrated according to the methods described (D. E. Nurse et al., *Br. J. Urol.*, v. 68 pp. 27–31 (1991); B. B. Howe et al., *J. Pharmacol. Exp. Ther.*, v. 274 pp. 884–890 (1995); K. Lawson, *Pharmacol. Ther.*, v. 70 pp. 39–63 (1996); D. R. Gehlert, et al., *Neuro-Psychopharmacol & Biol. Psychiat.*, v. 18 pp. 1093–1102 (1994); M. Gopalakrishnan et al., *Drug Development Research*, v. 28 pp. 95–127 (1993); J. E. Freedman et al., *The Neuroscientist*, v. 2 pp. 145–152 (1996); D. Spanswick et al., *Nature*, v. 390 pp. 521–25 (Dec. 4, 1997)).

Aqueous liquid compositions of the present invention are particularly useful for the treatment and prevention of asthma, epilepsy, hypertension, Raynaud's syndrome, impotence, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, more preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

We claim:
1. A compound of Formula I

$$\text{(Structure I: pyridine ring with substituents } R_1\text{-S(O)}_n\text{, } R_2\text{, A, } R_4\text{, NH, } R_5\text{)}$$

or a pharmaceutically acceptable salt, ester, amide, or prodrug thereof wherein
$R_1$ is alkyl;
$R_2$ is selected from the group consisting of aryl and heteroaryl;
the aryl or heteroaryl are optionally substituted;
n is 0–2;
A is selected from the group consisting of hydrogen, alkyl, and —X—$R_3$;
$R_3$ is alkyl or haloalkyl;
X is —C(O)— or —S(O)$_p$—;
p is 1–2;
$R_4$ and $R_5$ are independently selected from the group consisting of hydrogen, alkyl and haloalkyl; or
$R_1$ and $R_5$ together with the ring to which they are attached form a 5-, 6- or 7-membered sulfur-containing ring with 1–2 double bonds and 0–2 oxo substituents; or
A and $R_4$ together with the ring to which they are attached form a ring selected from the group consisting of a 5-, 6-, or 7-membered carbocyclic ring with 1–2 double bonds and 0–1 oxo substituents and a 5-, 6- or 7-membered sulfur-containing ring with 1–2 double bonds and 0–2 oxo substituents, provided that one of $R_1$ and $R_5$ or A and $R_4$ forms a ring.

2. The compound according to claim 1 wherein A and $R_4$ together with the ring to which they are attached form a 6-membered carbocyclic ring with 1 double bond and 1 oxo substituent.

3. The compound according to claim 2 wherein $R_1$ and $R_5$ are alkyl.

4. The compound according to claim 3 wherein $R_2$ is an optionally substituted aryl.

5. The compound according to claim 4 selected from the group consisting of
4-(3-cyanophenyl)-4,6,7,8-tetrahydro-2-methyl-3-(methylsulfonyl)-5(1H)-quinolinone;
4,6,7,8-tetrahydro-2-methyl-3-(methylsulfonyl)-4-(3-nitrophenyl)-5(1H)-quinolinone;
4,6,7,8-tetrahydro-2-methyl-3-(methylsulfonyl)-4-[4-(trifluoromethyl)phenyl]-5(1H)-quinolinone;
4-(3,4-dichlorophenyl)-4,6,7,8-tetrahydro-2-methyl-3-(methylsulfonyl)-5(1H)-quinolinone;
4,6,7,8-tetrahydro-2-methyl-4-(4-methyl-3-nitrophenyl)-3-(methylsulfonyl)-5(1H)-quinolinone;
4-(4-chloro-3-nitrophenyl)-4,6,7,8-tetrahydro-2-methyl-3-(methylsulfonyl)-5(1H)-quinolinone;
4-(3-bromo-4-fluorophenyl)-4,6,7,8-tetrahydro-2-methyl-3-(methylsulfonyl)-5(1H)-quinolinone;
4-(4-chloro-3-fluorophenyl)-4,6,7,8-tetrahydro-2-methyl-3-(methylsulfonyl)-5(1H)-quinolinone; and
4-(3,4,5-trifluorophenyl)-4,6,7,8-tetrahydro-2-methyl-3-(methylsulfonyl)-5(1H)-quinolinone.

6. The compound according to claim 1 wherein A and $R_4$ together with the ring to which they are attached form a 5-membered carbocyclic ring with 1 double bond and 1 oxo substituent.

7. The compound according to claim 1 wherein A is —X—$R_3$, X is —C(O)—, and $R_3$ and $R_4$ are alkyl.

8. The compound according to claim 7 wherein $R_1$ and $R_5$ together with the ring to which they are attached form a 6-membered sulfur-containing ring with 1 double bond and 2 oxo substituents.

9. The compound according to claim 8 wherein $R_2$ is an optionally substituted aryl.

10. The compound according to claim 9 selected from the group consisting of
1-[8-(3,4-dichlorophenyl)-3,4,5,8-tetrahydro-6-methyl-1,1-dioxido-2H-thiopyrano[3,2-b]pyridin-7-yl]ethanone; and
1-[8-(4-chloro-3-nitrophenyl)-3,4,5,8-tetrahydro-6-methyl-1,1-dioxido-2H-thiopyrano[3,2-b]pyridin-7-yl]ethanone.

11. The compound according to claim 1 wherein A and $R_4$ together with the ring to which they are attached form a 6-membered sulfur-containing ring with 1 double bond and 0–2 oxo substituents.

12. A method for treating a disease treatable with a potassium channel opener in a host mammal comprising administering to the host mammal in need thereof an effective amount of a potassium channel opening compound of claim 1.

13. The method of claim 12 wherein the disease is selected from the group consisting of asthma, epilepsy, hypertension, Raynaud's syndrome, impotence, migraine, pain, eating disorders, urinary incontinence, functional bowel disorders, neurodegeneration and stroke.

* * * * *